United States Patent
Filla et al.

[11] Patent Number: 5,998,622
[45] Date of Patent: Dec. 7, 1999

[54] 5-HT$_{1F}$ AGONISTS INTERMEDIATES

[75] Inventors: Sandra Ann Filla, Indianapolis; Kirk W. Johnson, Carmel; Lee A. Phebus, Fountaintown; John Mehnert Schaus, Zionsville, all of Ind.

[73] Assignee: Eli Lilly and Company, Indianapolis, Ind.

[21] Appl. No.: 09/112,562

[22] Filed: Jul. 9, 1998

Related U.S. Application Data

[62] Division of application No. 08/969,851, Nov. 14, 1997, Pat. No. 5,817,671
[60] Provisional application No. 60/030,950, Nov. 15, 1996.

[51] Int. Cl.⁶ .................................................. C07D 471/04
[52] U.S. Cl. ........................................... 546/113; 544/127
[58] Field of Search ............................................... 546/113

[56] References Cited

U.S. PATENT DOCUMENTS

| | | |
|---|---|---|
| 5,051,412 | 9/1991 | Macor . |
| 5,169,947 | 12/1992 | Macor . |
| 5,521,196 | 5/1996 | Audia et al. . |
| 5,521,197 | 5/1996 | Audia . |
| 5,604,240 | 2/1997 | Chambers et al. . |
| 5,708,008 | 1/1998 | Audia et al. . |

FOREIGN PATENT DOCUMENTS

| | | |
|---|---|---|
| 0379314 | 7/1990 | European Pat. Off. . |
| 2295615 | 6/1996 | United Kingdom . |
| WO 96/29075 | 9/1996 | WIPO . |

*Primary Examiner*—Robert W. Ramsuer
*Attorney, Agent, or Firm*—Robert D. Titus

[57] ABSTRACT

This invention provides 5-HT$_{1F}$ agonists of Formula I;

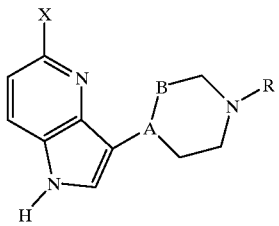

where A-B, X, and R are as defined in the specification. The invention also encompasses pharmaceutical formulations employing compounds of Formula I as well as methods of treating conditions associated with 5-HT$_{1F}$ activation employing these compounds or compositions. The invention also provides intermediates useful for the preparation of the compounds of Formula I.

2 Claims, No Drawings

5-HT$_{1F}$ AGONISTS INTERMEDIATES

CROSS-REFERENCE

This application is a divisional of application Ser. No. 08/969,851, filed Nov. 14, 1997 now U.S. Pat. No. 5,817,671. This application claims benefit of Provisional Application Ser. No. 60/030,950 filed Nov. 15, 1996.

BACKGROUND OF THE INVENTION

Serotonin (5-HT) exhibits diverse physiological activity mediated by at least seven receptor classes, the most heterogeneous of which appears to be 5-HT$_1$. A human gene which expresses on of these 5-HT$_1$ receptor sybtypes, named 5-HT$_{1F}$, was isolated by Kao and coworkers (*Proc. Natl. Acad. Sci. USA*, 90, 408–412 (1993)). This 5-HT$_{1F}$ receptor exhibits a pharmacological profile distinct from any serptonergic receptor yet described.

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers (*Neurology*, 43,(suppl. 3), S16–S20 (1993)). It has been demonstrated that agonists of the 5-HT$_{1F}$ receptor inhibit peptide extravasation due to stimulation of the trigeminal ganglia (Audia and Nissen, U.S. Pat. No. 5,521,196).

Compounds which exhibit affinity for the 5-HT$_{1F}$ receptor provide a new approach for the treatment of diseases linked to abnormal serotonergic neurotransmission. Furthermore, compounds selective for the 5-HT$_{1F}$ receptor subtype are potentially useful for treating such diseases while causing fewer undesired side effects.

SUMMARY OF THE INVENTION

The present invention provides 5-substituted-3-(piperidin-4-yl)- and 5-substituted-3-(1,2,3,6-tetrahydropyridin-4-yl)pyrrolo[3,2-b]pyridines of Formula I:

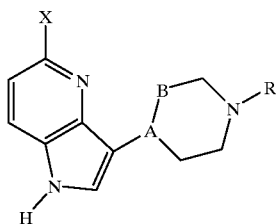

I in which

A-B is —C=CH— or —CH—CH$_2$—;
R is H, C$_1$–C$_6$ alkyl, benzyl, or phenylethyl;
X is —NR$^1$SO$_2$R$^2$, —NHC(Q)NR$^3$R$^4$, —NHC(O)OR$^5$, or —NR$^1$C(O)R$^6$ where:
Q is O, or S;
R$^1$ is H or C$_1$–C$_4$ alkyl;
R$^2$ is C$_1$–C$_4$ alkyl, phenyl or substituted phenyl;
R$^3$ and R$^4$ are independently selected from the group consisting of H, C$_1$–C$_6$ alkyl, C$_3$–C$_6$ alkenyl, C$_3$–C$_8$ cycloalkyl, phenyl, substututed phenyl, phenyl (C$_1$–C$_4$ alkylene), phenyl (C$_1$–C$_4$ alkylenyl) substituted in the phenyl ring, ((C$_1$–C$_4$ alkyl or C$_1$–C$_4$ alkoxycarbonyl substituted) C$_1$–C$_4$ alkyl)phenyl, C$_1$–C$_4$ alkyl α-substituted with C$_1$–C$_4$ alkoxycarbonyl, heteroaryl; or
R$^3$ and R$^4$ taken together with the nitrogen atom to which they are attached form a pyrrolidine, piperidine, piperazine, 4-substituted piperazine, morpholine or thiomorpholine ring;
R$^5$ is C$_1$–C$_6$ alkyl, C$_3$–C$_6$ alkenyl, phenyl, substituted phenyl, C$_3$–C$_8$ cycloalkyl, C$_1$–C$_4$ alkyl ω-substituted with C$_1$–C$_4$ alkoxy;
R$^6$ is C$_1$–C$_{10}$ alkyl, substituted C$_1$–C$_{10}$ alkyl, C$_2$–C$_{10}$ alkenyl, C$_2$–C$_{10}$ alkynyl, C$_3$–C$_8$ cycloalkyl, phenyl, substituted phenyl, naphthyl, phenyl(C$_1$–C$_4$ alkylene), phenyl(C$_1$–C$_4$ alkylene) substituted on the phenyl ring, 2-phenylethylen-1-yl, diphenylmethyl, benzofused C$_4$–C$_8$ cycloalkyl, C$_1$–C$_4$ alkylene ω-substituted with C$_3$–C$_6$ cycloalkyl, or a heterocycle; and pharmaceutically acceptable acid addition salts and solvates thereof.

This invention also provides a pharmaceutical formulation which comprises, in association with a pharmaceutically acceptable carrier, diluent or excipient, a compound of Formula I.

A further embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, general pain, chronic pain, post-traumatic syndrome, memory loss, dementia of aging, social phobia, attention deficit hyperactivity disorder, disruptive behavior disorders, impulse control disorders, borderline personality disorder, obsessive computsive disorder, chronic fatigue syndrome, premature ejaculation, erectile difficulty, anorexia nervosa, disorders of sleep, autism, mutism, allergic rhinitis, trichotillomania, trigeminal neuralgia, dental pain or temperomandibular joint dysfunction pain. The compounds of this invention are also useful as a prophylactic treatment for migraine. Any of these methods employ a compound of Formula I.

The use of a compound of Formula I for the activation of the 5-HT$_{1F}$ receptor, for the inhibition of peptide extravasation in general or due to stimulation of the trigeminal ganglia specifically, and for the treatment of any of the disorders described supra, are all embodiments of the present invention.

The present invention also includes intermediates useful for the preparation of compounds of Formula I.

DETAILED DESCRIPTION OF THE INVENTION

The general chemical terms used in the formulae above have their usual meanings. For example, the term "alkyl" includes such groups as methyl, ethyl, n-propyl, isopropyl, n-butyl, isobutyl, sec-butyl, tert-butyl, pentyl, 2-pent-yl-, 3-pentyl-, neopentyl, hexyl, heptyl, octyl and the like. The term "alkoxy" includes such groups as methoxy, ethoxy, isopropoxy, sec-butoxy, tert-butoxy, 2-pentoxy-, 3-hexyloxy, heptyloxy, octyloxy, and the like. The term "alkylthio" includes such groups as methylthio, ethylthio, isopropylthio, sec-butylthio, tert-butylthio, and the like. The term "aklenyl" includes vinyl, allyl, 1-buten-4-yl, 2-buten-4-yl, 1-penten-5-yl, 2-penten-5-yl, 3-penten-5-yl, 1-hexen-6-yl, 2-hexen-6-yl, 3-hexen-6-yl, 4-hexen-6-yl and the like. The term "alkynyl" includes acetylenyl, propynyl, 2-butyn-4-yl, 1-butyn-4-yl, 1-pentyn-5-yl, 2-pentyn-5-yl and the like. The term "acyl" includes, for example, formyl, acetyl, propanoyl, butanoyl, and 2-methylpropanoyl. The term "cycloalkyl" includes such groups as cyclopropyl, cyclobutyl, cyclopentyl, cyclohexyl, cycloheptyl and cyclooctyl. The term "phenyl($C_1$–$C_4$ alkylene)" includes such groups as benzyl, phenethyl, phenpropyl and phenbutyl. The term "($C_1$–$C_4$ alkyl)sulfonyl" includes methanesulfonyl, ethanesulfonyl propanesulfonyl, isopropanesulfonyl, butanesulfonyl and the like. The term "halo" includes fluoro, chloro, bromo and iodo.

The term "substituted alkyl" is taken to mean an alkyl moiety substituted with up to three substituents selected from the group consisting of hydroxy, $C_1$–$C_4$ alkoxy, halo, aryloxy, $C_1$–$C_4$ alkoxycarbonyl and heteroaryloxy.

The term "substituted phenyl" or "phenyl($C_1$–$C_4$ alkylene) substituted in the phenyl ring" is taken to mean the phenyl moiety may be substituted with one substituent selected from the group consisting of halo, $C_1$–$C_4$ alkyl, $C_1$–$C_8$ alkoxy, $C_1$–$C_4$ alkylthio, nitro, cyano, di($C_1$–$C_4$ alkyl)amino, trifluoromethyl, trifluoromethoxy, phenyl, $C_1$–$C_4$ acyl, benzoyl or ($C_1$–$C_4$ alkyl)sufonyl, or two to three substituents independently selected from the group consisting of halo, nitro, $C_1$–$C_4$ alkyl, or $C_1$–$C_4$ alkoxy.

The term "heterocycle" is taken to mean stable aromatic and non-aromatic 5- and 6-membered rings containing carbon and from 1 to 3 heteroatoms selected from the group consisting of nitrogen, oxygen and sulfur, said rings being optionally monobenzofused. All of these rings may be substituted with up to three substituents independently selected from the group consisting of halo, $C_1$–$C_4$ alkoxy, $C_1$–$C_4$ alkyl, cyano, nitro, hydroxy, —S(O)$_n$—($C_1$–$C_4$ alkyl) and —S(O)$_n$-phenyl where n is 0, 1 or 2. Where tautomers are possible, all tautomeric forms are contemplated by the present invention. Non-aromatic rings include, for exampke, pyrrolidinyl, piperidinyl, piperazinyl, tetrahydrofuryl, oxazolidinyl, dioxanyl, pyranyl, and the like. Benzofused non-aromatic rings include indolinyl, 1,2,3,4-tetrahydroquinolinyl, 1,2,3,4-tetrahydroisoquinolinyl and the like. Aromatic rings include furyl, thienyl, pyridinyl, pyridinyl-N-oxide, pyrrolyl, N-methylpyrrolyl, oxazolyl, isoxazolyl, pyrazolyl, imidazolyl, triazolyl, oxadiazolyl, thiadiazolyl, thiazolyol, pyrimidinyl, pyrazinyl, pyridazinyl, and the like. Benzofused aromatic rings include isoquinolinyl, isoquinolinyl-N-oxide, benzoxazolyl, benzthiazolyl, quinolinyl, quinolinyl-N-oxide, benzofuranyl, thionaphthyl, indolyl and the like.

The term "heteroaryl" is taken to mean an aromatic or benzofused aromatic heterocycle as defined in the previous paragraph. The term "substituted heteroaryl" is taken to mean an aromatic or benzofused aromatic heterocycle as defined in the previous paragraph substituted with up to three substituents independently selected from the group consisting of halo, $C_1$–$C_4$ alkoxy, $C_1$–$C_4$ alkyl, cyano, nitro, hydroxy, —S(O)$_n$—($C_1$–$C_4$ alkyl) and —S(O)$_n$-phenyl where n is 0, 1 or 2. Where tautomers are possible, all tautomeric forms are contemplated by the present invention. The term "heteroaryl($C_1$–$C_4$ alkyl) is taken to mean a branched or linear alkyl chain of 1 to 4 carbon atoms substituted at some point with an aromatic or benzofused aromatic heterocycle moiety. The term "substituted heteroaryl($C_1$–$C_4$ alkyl)" is taken to mean a branched or linear alkyl chain of 1 to 4 carbon atoms substituted at some point with an aromatic or benzofused aromatic heterocycle moiety which is substituted with up to three substituents independently selected from the group consisting of halo, $C_1$–$C_4$ alkoxy, $C_1$–$C_4$ alkyl, cyano, nitro, hydroxy, —S(O)$_n$—($C_1$–$C_4$ alkyl) and —S(O)$_n$-phenyl where n is 0, 1 or 2.

The term "heteroaryloxy" is taken to mean a heteroaryl or substituted heteroaryl group, as defined in the previous paragraph, bonded to an oxygen atom.

The term "aryloxy" is taken to mean a phenyl or substituted phenyl group bonded to an oxygen atom.

The term "4-substituted piperazine" is taken to mean a piperazine ring substituted at the 4-position with a substituent selected from the group consisting of $C_1$–$C_6$ alkyl, $C_1$–$C_4$ alkoxy substituted $C_1$–$C_6$ alkyl, phenyl, substituted phenyl, phenyl($C_1$–$C_4$ alkylene), phenyl ($C_1$–$C_4$ alkylene) substituted in the phenyl ring, heteroaryl, and heteroaryl ($C_1$–$C_4$ alkylene).

The term "benzofused $C_4$–$C_8$ cycloalkyl" is taken to mean a $C_4$–$C_8$ cycloalkyl group fused to a phenyl ring. Examples of these groups include benzocyclobutyl, indanyl, 1,2,3,4-tetrahydronaphthyl, and the like.

While all of the compounds of this invention are useful as 5-HT$_{1F}$ agonists, certain classes are preferred. The following paragraphs describe such preferred classes.

aa) R is hydrogen;
ab) R is methyl;
ac) X is —NR$^1$SO$_2$R$^2$;
ad) X is —NHC(Q)NR$^3$R$^4$;
ae) X is —NHC(O)OR$^5$;
af) X is —NR$^1$C(O)R$^6$;
ag) Q is O;
ah) R$^1$ is H;
ai) R$^2$ is phenyl:
aj) R$^3$ is H;
ak) R$^4$ is $C_1$–$C_4$ alkyl;
al) R$^4$ is methyl;
am) R$^4$ is phenyl;
an) R$^4$ is $C_3$–$C_8$ alkenyl;
ao) R$^4$ is allyl;
ap) R$^4$ is phenyl monosubstituted with halo;
aq) R$^4$ is 4-fluorophenyl;
ar) R$^4$ is heteroaryl;
as) R$^4$ is 4-pyridyl;
at) R$^5$ is methyl;
au) R$^5$ is methyl;
av) R$^5$ is ethyl;
aw) R$^5$ is propyl;
ax) R$^6$ is $C_1$–$C_{10}$ alkyl;
ay) R$^6$ is $C_1$–$C_4$ alkyl;
az) R$^6$ is methyl;
ba) R$^6$ is ethyl;
bb) R$^6$ is propyl;
bc) R$^6$ is $C_3$–$C_6$ alkenyl;
bd) R$^6$ is allyl;
be) R$^6$ is $C_3$–$C_6$ cycloalkyl;
bf) R$^6$ is cyclopropyl;
bg) R$^6$ is cyclobutyl;
bd) R$^6$ is phenyl;
be) R$^6$ is phenyl monosubstituted with halo;

bf) $R^6$ is phenyl monosubstituted with fluoro;

bg) $R^6$ is 4-fluorophenyl;

bh) $R^6$ is phenyl monosubstituted with nitro;

bi) $R^6$ is phenyl monosubstituted with cyano;

bj) $R^6$ is 4-nitrophenyl;

bk) $R^6$ is 4-cyanophenyl;

bl) $R^6$ is heterocycle;

bm) $R^6$ is furyl optionally substituted with $C_1$–$C_4$ alkyl, $C_1$–$C_4$ alkoxy, or halo;

bn) $R^6$ is 3-furyl;

bo) $R^6$ is thienyl optionally substituted with halo, $C_1$–$C_4$ alkyl or $C_1$–$C_4$ alkoxy;

bp) $R^6$ is 3-thienyl;

bq) $R^6$ is pyridinyl optionally substituted with halo, $C_1$–$C_4$ alkyl or $C_1$–$C_4$ alkoxy;

br) $R^6$ is 4-pyridinyl;

bs) A-B is —C=CH—;

bt) A-B is —C—$CH_2$—;

bu) The compound is a free base;

bv) The compound is a salt;

bw) The compound is the hydrochloride salt;

bx) The compound is the fumarate salt.

It will be understood that the above classes may be combined to form additional preferred classes.

The compounds of the present invention may, depending upon their structure and manner of synthesis and isolation, exist as a pharmaceutically acceptable solvate. These solvates include water, methanol, and ethanol. Solvated forms of the compounds of the present invention represent a further embodiment of the present invention.

The compounds of this invention are useful in a method for increasing activation of the 5-$HT_{1F}$ receptor for treating a variety of disorders which have been linked to decreased neurotransmission of serotonin in mammals. It is preferred that the mammal to be treated by the administration of compounds of this invention is human.

Since the compounds of this invention are amines, they are basic in nature and accordingly react with any of a number of inorganic and organic acids to form pharmaceutically acceptable acid addition salts. It is preferable to convert the free amines to their pharmaceutically acceptable acid addition salts for ease of handling and administration. Acids commonly employed to form such salts are inorganic acids such as hydrochloric acid, hydrobromic acid, hydroiodic acid, sulfuric acid, phosphoric acid, and the like, and organic acids, such as p-toluene-sulfonic acid, methanesulfonic acid, oxalic acid, p-bromo-phenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monogydrogenphosphate, dihydrogenphosphate, metaphosphate, pyrophosphate, chloride, bromide, iodide, acetate, pripionate, decanoate, caprylate, acrylate, formate, isoburyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-fulsonate, mandelate and the like. Preferred pharmaceutically acceptable salts are those formed with hydrochloric acid or fumaric acid.

The following group is illustrative of compounds contemplated within the scope of this invention:

N-propyl-N'-(3-(1-(2-pentyl)-1,2,3,4-tetrahydropyridin-4-yl)pyrrolo[3,2-b]pyridin-5-yl)thiourea decanoate N-butyl-N'-(3-(1-isopropylpiperidin-4-yl)pyrrolo[3,2-b]pyridin-5-yl)thiourea acrylate N-(2-methoxy)phenyl-N'-(3-(1-(sec-butyl)-1,2,3,4-tetrahydropyridin-4-yl)pyrrolo[3,2-b]pyridin-5-yl)thiourea formate N-(4-propoxy)phenyl-N'-(3-(1-ethylpiperidin-4-yl)-pyrrolo[3,2-b]pyridin-5-yl)thiourea isobutyrate N-(2-butoxy)phenyl-N'-(3-(1-hexylpiperidin-4-yl)pyrrolo[3,2-b]pyridin-5-yl)thiourea fumarate N-(2,3-dibromo)phenyl-N'-(3-(1-isopropylpiperidin-4-yl)pyrrolo[3,2-b]pyridin-5-yl)thiourea caproate N-(2-bromo-3-iodo)phenyl-N'-(3-(1-(2-pentyl)piperidin-4-yl)pyrrolo[3,2-b]pyridin-5-yl)thiourea heptanoate N-(3-phenpropyl)-N'-(3-(1-(sec-butyl)piperidin-4-yl)pyrrolo[3,2-b]pyridin-5-yl)thiourea propiolate N-(4-trifluoromethyl)phenyl-N'-(3-(1-neopentyl-1,2,3,4-tetrahydropyridin-4-yl)pyrrolo[3,2-b]pyridin-5-yl)thiourea oxalate N-(4-phenyl)phenyl-N'-(3-(1-pentylpiperidin-4-yl)pyrrolo[3,2-b]pyridin-5-yl)thiourea malonate N-hexyl-N'-(3-(1-propylpiperidin-4-yl)pyrrolo[3,2-b]pyridin-5-yl)urea succinate N-(2-buten-4-yl)-N'-(3-(1-butylpiperidin-4-yl)pyrrolo-[3,2-b]pyridin-5-yl)urea suberate N-(3-hexen-6-yl)-N'-(3-(1-(3-pentyl)piperidin-4-yl)-pyrrolo[3,2-b]pyridin-5-yl)urea sebacate N-cyclopropyl-N'-(3-(1-hexyl-1,2,3,4-tetrahydropyridin-4-yl)pyrrolo[3,2-b]pyridin-5-yl)urea fumarate N-cyclopentyl-N'-(3-(1-(3-pentyl)piperidin-4-yl)-pyrrolo[3,2-b]pyridin-5-yl)urea maleate N-cyclooctyl-N'-(3-(1-(tert-butyl)piperidin-4-yl)-pyrrolo[3,2-b]pyridin-5-yl)urea mandelate N-(3-phenyl)phenyl-N'-(3-(1-propyl-1,2,3,4-tetrahydropyridin-4-yl)pyrrolo[3,2-b]pyridin-5-yl)urea butyne-1,4-dioate N-(2-ethoxy)phenyl-N'-(3-(1-neopentylpiperidin-4-yl)-pyrrolo[3,2-b]pyridin-5-yl)urea hexyne-1,6-dioate N-(4-isopropoxy)phenyl-N'-(3-(1-isobutylpiperidin-4-yl)pyrrolo[3,2-b]pyridin-5-yl)urea benzoate N-(2-formyl)phenyl-N'-(3-(1-(3-pentyl)piperidin-4-yl)pyrrolo[3,2-b]pyridin-5-yl)urea 4-chlorobenzoate N-(3-propanoyl)phenyl-N'-(3-(1-pentylpiperidin-4-yl)pyrrolo[3,2-b]pyridin-5-yl)urea 2-methylbenzoate N-(3-ethylthio)phenyl-N'-(3-(1-propylpiperidin-4-yl)pyrrolo[3,2-b]pyridin-5-yl)urea 2,4-dinitrobenzoate N-(3-isopropylthio)phenyl-N'-(3-(1-isopropylpiperidin-4-yl)pyrrolo[3,2-b]pyridin-5-yl)urea 3-hydroxybenzoate N-(2-methyl)phenyl-N'-(3-(1-propylpiperidin-4-yl)pyrrolo[3,2-b]pyridin-5-yl)urea 4-methoxybenzoate N-(3-isopropyl)phenyl-N'-(3-(1-isopropylpiperidin-4-yl)pyrrolo[3,2-b]pyridin-5-yl)urea phthalate N-(2-ethoxycarbonyl)phenyl-N'-(3-(1-(tert-butyl)-piperidin-4-yl)pyrrolo[3,2-b]pyridin-5-yl)urea sulfonate N-(2-butoxycarbonyl)phenyl-N'-(3-(1-propylpiperidin-4-yl)pyrrolo[3,2-b]pyridin-5-yl)urea N-(3,4-difluoro)phenyl-N'-(3-(1-butylpiperidin-4-yl)-pyrrolo[3,2-b]pyridin-5-yl)urea N-(3-chloro-4-bromo)phenyl-N'-(3-(1-(3-pentyl)piperidin-4-yl)pyrrolo[3,2-b]pyridin-5-yl)urea N-(3-phenpropyl)-N'-(3-(1-propylpiperidin-4-yl)-pyrrolo[3,2-b]pyridin-5-yl)urea N-ethyl-N-phenyl-N'-(3-(1-butylpiperidin-4-yl)pyrrolo[3,2-b]pyridin-5-yl)urea N-isopropyl-N-phenyl-N'-(3-(1-(sec-butyl)piperidin-4-yl)pyrrolo[3,2-b]pyridin-5-yl)urea N-ethyl-N-methyl-N'-(3-(1-(2-pentyl)piperidin-4-yl)pyrrolo[3,2-b]pyridin-5-yl)urea N-methyl-N-isopropyl-N'-(3-(1-butylpiperidin-4-yl)pyrrolo[3,2-b]pyridin-5-yl)urea N,N-diisopropyl-N'-(3-(1-butylpiperidin-4-yl)pyrrolo[3,2-b]pyridin-5-yl)urea 5-butoxycarbonylamino-3-(1-propyl-1,2,3,4-tetrahydropyridin-4-yl)pyrrolo[3,2-b]pyridine 5-(2-buten-4-yloxy)carbonylamino-3-(-1,2,3,4-tetrahydropyridin-4-yl)pyrrolo[3,2-b]pyridine 5-(2-penten-5-yloxy)carbonylamino-3-(1-(sec-butyl)-piperidin-4-yl)pyrrolo[3,2-b]pyridine 5-(3-chlorophenoxy)carbonylamino-3-(1-hexylpiperidin-4-yl)pyrrolo[3,2-b]pyridine 5-(2-methoxyphenoxy)carbonylamino-3-(1-hexylpiperidin-4-yl)pyrrolo[3,2-b]pyridine 5-(3-butoxyphenoxy)carbonylamino-3-(1-neopentylpiperidin-4-yl)pyrrolo[3,2-b]pyridine 5-cyclopropoxycarbonylamino-3-(1-(tert-butyl)piperidin-4-yl)pyrrolo[3,2-b]pyridine 5-cyclohexyloxycarbonylamino-3-(1-isobutylpiperidin-4-yl)pyrrolo[3,2-b]pyridine 5-cyclooctyloxycarbonylamino-3-(1-isopropylpiperidin-4-yl)pyrrolo[3,2-b]pyridine 5-(propoxyethoxy)carbonylamino-3-(1-ethylpiperidin-4-yl)pyrrolo[3,2-b]pyridine 5-(4-methoxybutoxy)carbonylamino)1-ethylpiperidin-4-yl)pyrrolo[3,2-b]pyridine 5-(propanoyl)amino-3-(1-neopentylpiperidin-4-yl)pyrrolo[3,2-b]pyridine mandelate 5-(2-methylpropanoyl)amino-3-(1-(3-pentyl)piperidin-4-yl)pyrrolo[3,2-b]pyridine 5-(2-methyl-4-butyn-1-oyl)amino-3-(1-(tert-butyl)piperidin-4-yl)pyrrolo[3,2-b]pyridine 5-(2-methylbutanoyl)-N-methylamino-3-(1-ethylpiperidin-4-yl)pyrrolo[3,2-b]pyridine phenylacetate 5-(hex-3-enoyl)amino-3-(1-propylpiperidin-4-yl)pyrrolo[3,2-b]pyridine 5-(cycloheptylcarbonyl)amino-3-(1-butylpiperidin-4-yl)pyrrolo[3,2-b]pyridine phenylpropionate 5-(4-phenylbutanoyl)amino-3-(1-isopropyl-1,2,3,4-tetrahydropyridin-4-yl)pyrrolo[3,2-b]pyridine phenylbutyrate 5-(5-phenoxypentanoyl)amino-3-(1-neopentyl-1,2,3,4-tetrahydropyridin-4-yl)pyrrolo[3,2-b]pyridine citrate 5-(5-methoxypentanoyl)amino-3-(1-isopropylpiperidin-4-yl)pyrrolo[3,2-b]pyridine lactate 5-((3-propoxycarbonyl)propanoyl)amino-3-(1-isobutylpiperidin-4-yl)pyrrolo[3,2-b]pyridine 5-((5-methoxycarbonyl)pentanoyl)amino-3-(1-isobutylpiperidin-4-yl)pyrrolo[3,2-b]pyridine β-hydroxybutyrate 5-(benzoyl-N-ethyl)amino-3-(1-ethylpiperidin-4-yl)pyrrolo[3,2-b]pyridine glycollate 5-benzoylamino-3-(1-propylpiperidin-4-yl)pyrrolo[3,2-b]pyridine tartrate 5-benzoylamino-3-(1-isopropylpiperidin-4-yl)pyrrolo[3,2-b]pyridine 5-benzoylamino-3-(1-(tert-butyl)-1,2,3,4-tetrahydropyridin-4-yl)pyrrolo[3,2-b]pyridine hydrochloride 5-(4-fluorobenzoyl)amino-3-(1-ethyl-1,2,3,4-tetrahydropyridin-4-yl)pyrrolo[3,2-b]pyridine 5-(4-(formyl)benzoyl)amino-3-(1-(sec-butyl)piperidin-4-yl)pyrrolo[3,2-b]pyridine 5-(3-(butanoyl)benzoyl)amino-3-(1-methylpiperidin-4-yl)pyrrolo[3,2-b]pyridine 5-(2-(benzoyl)benzoyl)amino-3-(1-pentylpiperidin-4-yl)pyrrolo[3,2-b]pyridine 5-(2-methanesulfonyl)benzoyl)amino-3-(1-butylpiperidin-4-yl)pyrrolo[3,2-b]pyridine 5-(3-phenylbenzoyl)amino-3-(1-(tert-butyl)piperidin-4-yl)pyrrolo[3,2-b]pyridine 5-(2,3-dibromo)benzoyl-N-isopropylamino-3-(1-isopropylpiperidin-4-yl)pyrrolo[3,2-b]pyridine 5-(2-bromo-3-iodo)benzoylamino-3-(1-(2-pentyl)piperidin-4-yl)pyrrolo[3,2-b]pyridine 5-(2-thiophenecarbonyl)-N-butylamino-3-(1-ethylpiperidin-4-yl)pyrrolo[3,2-b]pyridine 5-(2-thiophehecarbonyl)amino-3-(1-isopropylpiperidin-4-yl)pyrrolo[3,2-b]pyridine 5-(2-thiophehecarbonyl)amino-3-(1-tert-butyl)piperidin-4-yl)pyrrolo[3,2-b]pyridine 5-(2-thiophehecarbonyl)amino-3-(1-hexylpiperidin-4-yl)pyrrolo[3,2-b]pyridine 5-(3-thiophenecarbonyl)amino-3-(1-ethylpiperidin-4-yl)pyrrolo[3,2-b]pyridine 5-(2-furoyl)amino-3-(1-isopropyl-1,2,3,4-tetrahydropyridin-4-yl)pyrrolo[3,2-b]pyridine 5-(2-furoyl)amino-3-(1-butyl-1,2,3,4-tetrahydropyridin-4-yl)pyrrolo[3,2-b]pyridine 5-(2-furoyl)amino-3-(1-neopentylpiperidin-4-yl)pyrrolo[3,2-b]pyridine 5-(3-furoyl)amino-3-(1-butylpiperidin-4-yl)pyrrolo[3,2-b]pyridine 5-(2-pyridinecarbonyl)amino-3-(1-butylpiperidin-4-yl)pyrrolo[3,2-b]pyridine 5-(2-chloro-4-pyridinecarbonyl)amino-3-(1-methylpiperidin-4-yl)pyrrolo[3,2-b]pyridine 5-(3-pyrrolecarbonyl)amino-3-(1-methylpiperidin-4-yl)pyrrolo[3,2-b]pyridine 5-(2-oxazolecarbonyl)amino-3-(1-hexylpiperidin-4-yl)pyrrolo[3,2-b]pyridine 5-(2-methyl-4-oxazolecarbonyl)amino-3-(1-methylpiperidin-4-yl)pyrrolo[3,2-b]pyridine 5-(4-pyrazolecarbonyl)amino-3-(1-methylpiperidin-4-yl)pyrrolo[3,2-b]pyridine 5-(5-isoxazolecarbonyl)amino-3-(1-methylpiperidin-4-yl)pyrrolo[3,2-b]pyridine 5-(3-imidazolecarbonyl)amino-3-(1-methylpiperidin-4-yl)pyrrolo[3,2-b]pyridine 5-(2-methoxy-4-pyrimidinecarbonyl)amino-3-(1-methylpiperidin-4-yl)pyrrolo[3,2-b]pyridine 5-(2-quinolinecarbonyl)amino-3-(1-methylpiperidin-4-yl)pyrrolo[3,2-b]pyridine 5-(2-cyano-5-quinolinecarbonyl)amino-3-(1-methylpiperidin-4-yl)pyrrolo[3,2-b]pyridine The compounds of this invention are prepared by reacting an appropriate 5-aminopyrrolo[3,2-b]pyridine of formula II with a suitable electrophile by methods well known to one of ordinary skill in the art. This chemistry is described in Synthetic Scheme I where R' is $C_1$–$C_4$ alkyl, ($C_1$–$C_4$ alkoxy)carbonyl, benzyl, or phenylethyl, and A-B and $R^1$–$R^6$ are as previously defined.

Synthetic Scheme I

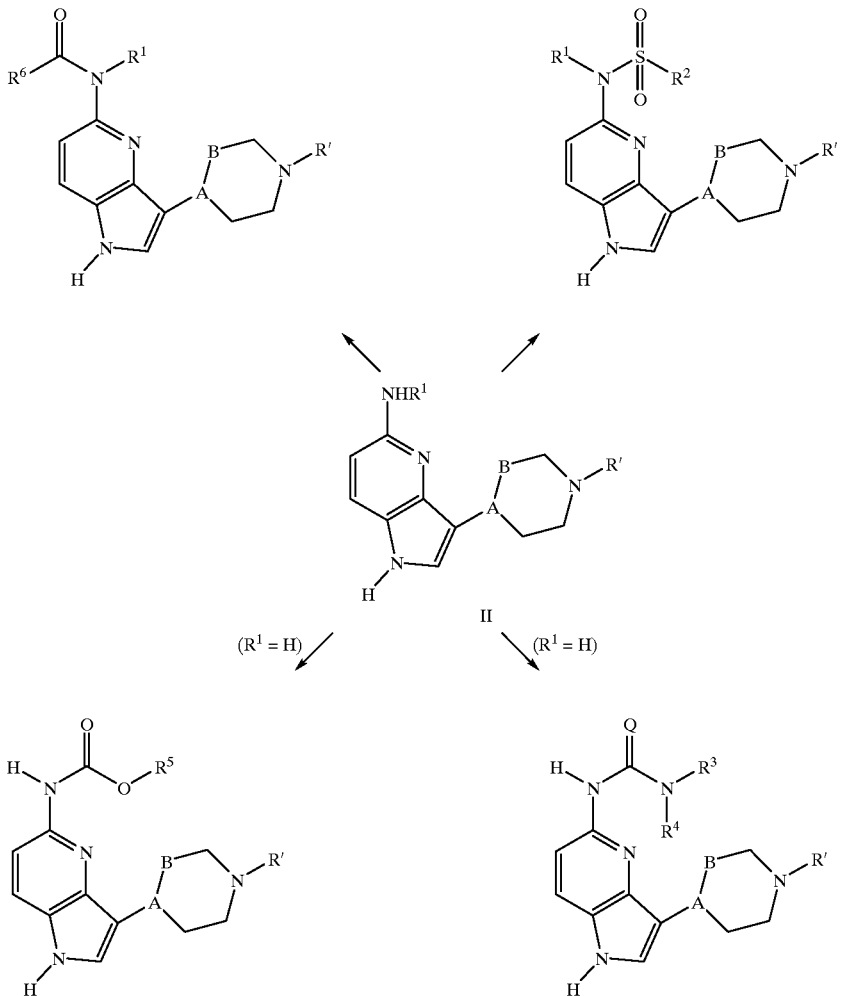

The compounds of the invention where X is —NR$^1$SO$_2$R$^2$ may be prepared by reacting a 5- aminopyrrolo[3,2-b]pyridine with an appropriate sulfonyl halide or anhydride to give the corresponding sulfonamide. A solution of the 5-aminopyrrolo[3,2-b]pyridine in a suitable solvent, such as pyridine, tetrahydrofuran, dioxane, diethyl ether or dimethylformamide, at a temperature from about ambient to about 0° C., is reacted with a commercially available R$^2$-sulfonyl halide or R$^2$-sulfonic anhydride in the presence of a suitable base such as puyridine or triethylamine. The resultant sulfonamide is isolated by normal extractive workup and the product purified by chromatography, or by recrystallization from a suitable solvent. The skilled artisan will appreciate that when pyridine is used as solvent, no additional base is required.

Compounds of the invention where X is —NHC(Q)NR$^3$R$^4$ are prepared by treating a solution of the 5-aminopyrrolo[3,2-b]pyridine in a suitable solvent, such as tetrahydrofuran, dimethylformamide, chloroform or dichloromethane, with an appropriate isocyanate, isothiocyanate, carbamoyl chloride or carbamoyl bromide. Appropriate carbamoyl chlorides are available by treating an amine of formula HNR$^3$R$^4$ with phosgene. When a carbamoyl chloride or carbamoyl bromide is used, the reactions are performed in the presence of a suitable base. Suitable bases include amines typically used as acid scavengers, such as pyridine or triethylamine, or commercially available polymer bound bases such as polyvinylpyridine. If necessary, an excess of the isocyanate, isothiocyanate, carbamoyl chloride or carbamoyl bromide is employed to ensure complete reaction of the starting amine. The reactions are performed at about ambient to about 80° C., for from about three hours to about three days. Typically, the product may be isolated by washing the reaction mixture with water and concentrating the remaining organics under reduced pressure. When an excess of isocyanate, isothiocyanate, carbamoyl chloride or carbamoyl bromide has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired. The skilled artisan will appreciate that compounds of the invention which are ureas may be converted into the corresponding thiourea by treatment with [2,4-bis(4-methoxyphenyl)-1,3-dithia-2,4-diphosphetane-2,4-disulfide] (Lawesson's Reagent) or phosphorus pentasulfide.

Compounds of the invention where X is —NHC(O)OR$^5$ are prepared by reacting the 5-aminopyrrolo[3,2-b]pyridine with an appropriately substituted chloroformate in the presence of an acylation catalyst such as dimethylaminopyridine, in the presence of a suitable base, such as those described supra. Alternatively, the reaction may be performed in pyridine, which serves as solvent and base. Under certain circumstances, diacylation of the 5-amino moiety may occur. Treatment of the diacylated product with hydrochloric acid at room temperature provides the monoacylated products of the present invention.

Compounds of the invention where X is —NR$^1$C(O)R$^6$ may also be prepared by reacting the 5-aminopyrrolo[3,2-b]pyridine with an appropriate carboxylic acid in the presence of typical peptide coupling reagents such as N-N'-carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (*Tetrahedron Letters*, 34(48), 7685 (1993)) and is very useful for the preparation of the compounds of the present invention. The product from these reactions is isolated and purified as described above.

The skilled artisan will appreciate that compounds of the invention where R is hydrogen may be prepared by removal of rppropriate R' substituents. Where R' is benzyl, for example, it may be removed by hydrogenolysis. Where R' is ($C_1$–$C_4$ alkoxy)carbonyl, it may be removed by hydrolysis. A particularly useful moiety for these purposes is the tert-butoxycarbonyl moiety which may be removed by treatment with trifluoroacetic acid at room temperature.

The 5-amino-3-(1,2,3,6-tetrahydropyridin-4-yl)pyrrolo[3,2-b]pyridines (VI) and 5-amino-3-(piperidin-4-yl)pyrrolo[3,2-b]pyridines (VII) required to prepare the compounds of the present invention are novel and represent a further embodiment of the present invention. Those 5-amino-3-(piperidin-4-yl)pyrrolo[3,2-b]pyridines of Formula II where R$^1$ is H (Formula IIa), may be prepared as described in Synthetic Scheme II, where R is as previously defined.

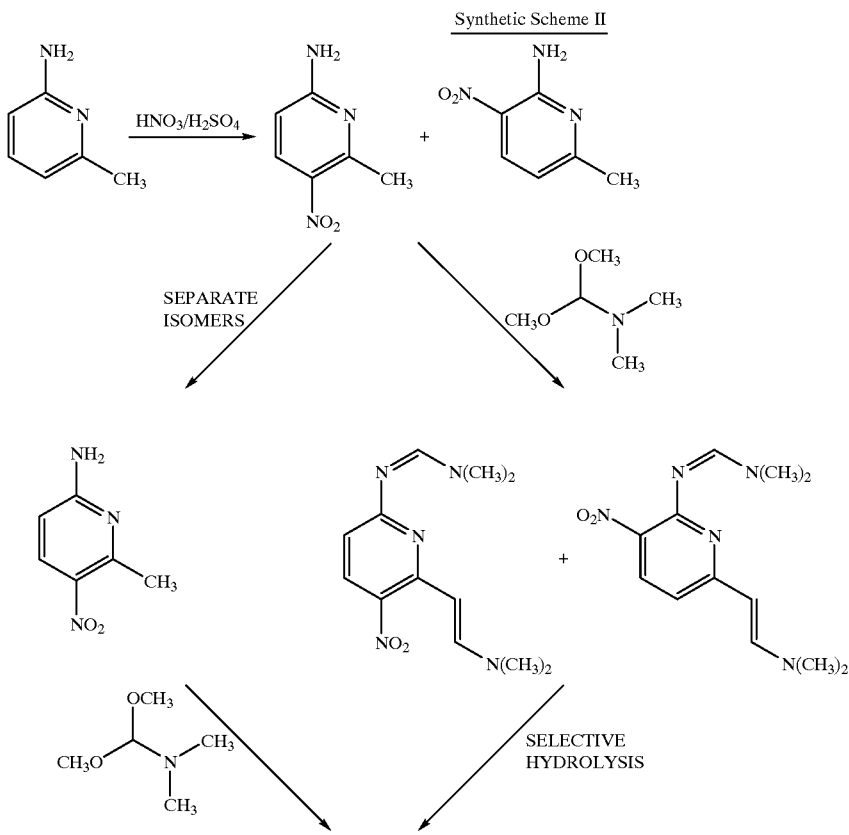

Synthetic Scheme II

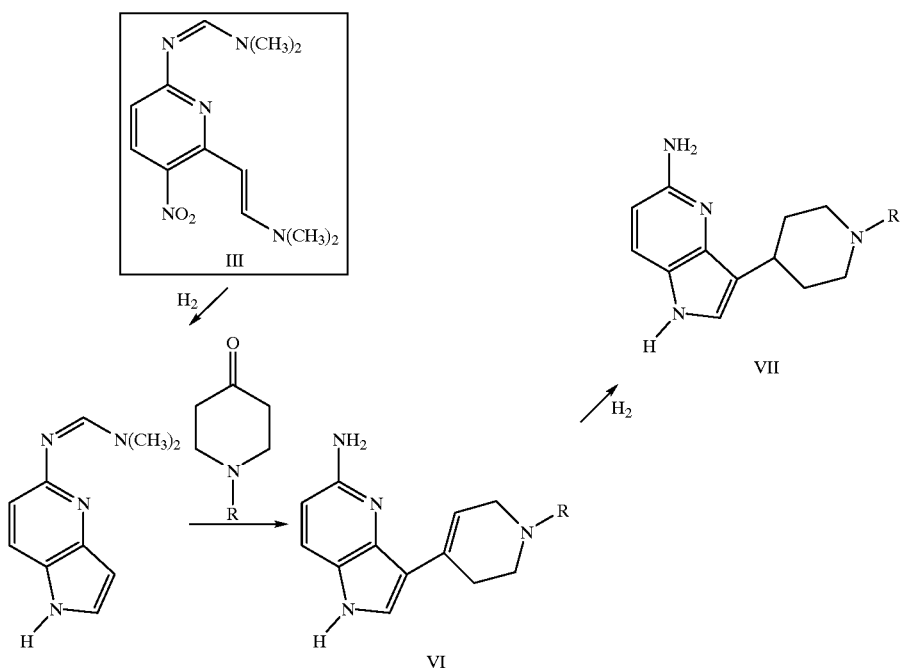

The nitration is performed by adding an equivalent of 90% nitric acid dissolved in an equal volume of concentrated sulfuric acid which has been precooled 0° C. to a solution of 6-amino-2-picoline (6-amino-2-methylpyridine) in five volumes (relative to volume of nitric acid solution) of concentrated sulfuric acid at −6° C. The nitric acid solution is added at a rate to maintain the temperature of the reaction mixture at about −2° C. The reaction mixture is stirred at about 0° C. for one hour and is then allowed to warm to about 10° C. over an hour. The temperature of the reaction mixture is maintained at about 10° C. for one hour and is then allowed to warm to about 20° C. over an hour. The reaction mixture is maintained at about 20° C. for 2 hours. The reaction mixture is then pooured over ice, made basic (pH about 9) by the addition of an appropriate hydroxide base, typically potassium, sodium, or ammonium hydroxide, maintaining the temperature at about 20° C. by the addition of ice as needed. The resulting slurry is filtered, washed with water, and dried to provide a 2:1 mixture of 3-nitro-:5-nitro-6-amino-2-picoline.

The undesired 5-nitro-6-amino-2-picoline isomer may be removed by steam distillation, sublimation, or by fractional crystallization from a suitable solvent, preferably toluene. The desired 3-nitro-6-amino-2-picoline is then reacted with dimethylformamide dimethylacetal or tris(dimethylamino)methane in a suitable solvent, typically dimethylformamide. Once the reaction is complete the reaction mixture is treated with either water or isopropanol to precipitate the desired intermediate III, which is isolated by filtration. Alternatively, Intermediate III may be prepared by directly subjecting the mixture of nitration isomers previously described to dimethylformamide dimethylacetal or tris(dimethylamino)methane. Treatment of the resulting reaction mixture with water results in the precipitation of Intermediate III which may be isolated by filtration.

Intermediate III may then be hydrogenated in a lower alkanol, typically ethanol, in the presence of a palladium catalyst, typically 10% palladium on carbon. Once hydrogenation is complete, the reaction mixture is filtered and the filtrate concentrated under reduced pressure. The desired 5-(dimethylaminomethylimino)pyrrolo[3,2-b]pyridine may be used as recovered in subsequent reactions or first purified by slurry washing or by silica gel chromatography as necessary or desired. Reacting 5-(dimethylaminoethylimino)pyrrolo[3,2-b]pyridine to an appropriately substituted 4-piperidinone in the presence of a suitable base, typically potassium or sodium hydroxide or alkoxide, in a suitable solvent, typically ethanol or methanol, provides the requisite Intermediate VI. Subjecting Intermediate VI to standard hydrogenation conditions provides Intermediate VII.

Alternatively, Intermediate VII may be prepared by the procedure described in Synthetic Scheme III.

Synthetic Scheme III

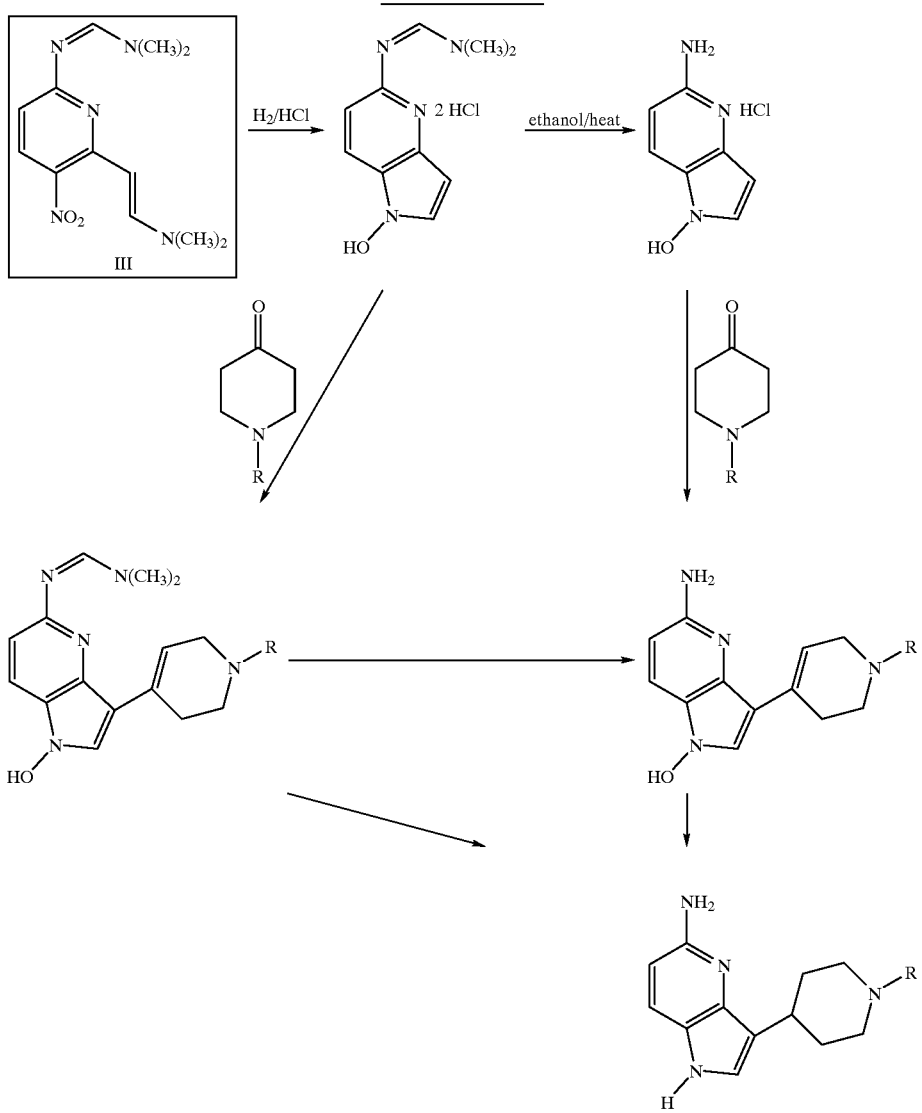

Intermediate III is hydrogenated in methanol containing hydrogen chloride in the presence of a palladium catalyst, typically 10% palladium on carbon. The resulting 1-hydroxy-5-(dimethylaminomethaneimino)pyrrolo[3,2-b] pyridine dihydrochloride is isolated by filtration of the reaction mixture and may be further purified and removed from catalyst by recrystallization. The amidine functionality at the 5-position of the pyrrolo[3,2-b]pyridine may be removed to provide the corresponding amine by heating the amidine substrate in ethanol under acidic conditions or under neutral hydrogenation conditions. The amidine functionality at the 5-position may be removed either prior or subsequent to reaction with an appropriate 4-piperidone.

Regardless of when the amidine functionality is removed, the 1-hydroxy substituent is removed by hydrogenation in a lower alkanol, typically methanol, in the presence of a palladium catalyst, typically 10% palladium on carbon.

Compounds of formula II where $R^1$ is lower alkyl are prepared by functionalizing the amino moiety by an acylation/reduction or reductive alkylation. This chemistry is illustrated in Synthetic Scheme IV, where M is methoxy, ethoxy, methyl, ethyl, propyl, or isopropyl, LG is chloro or bromo, $R^{1'}$ is $C_1$–$C_4$ alkyl, and A-B and R' are as defined supra.

Synthetic Scheme IV

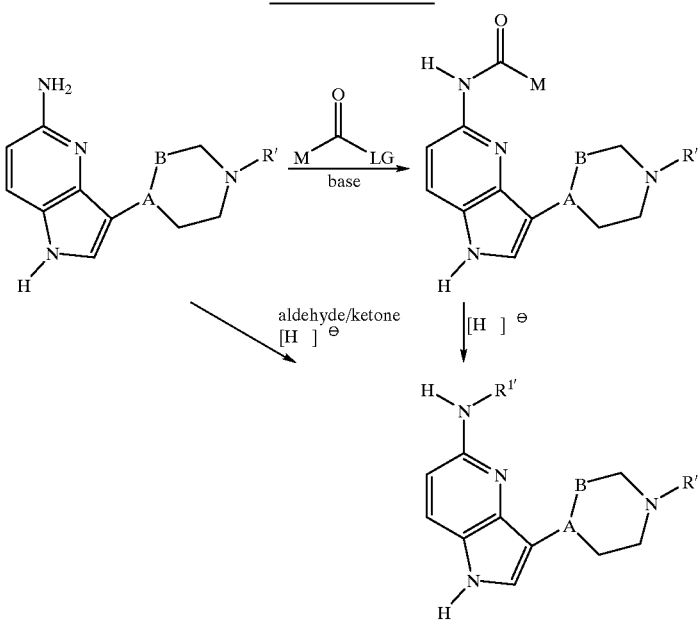

A solution of the 5-amino-pyrrolo[3,2-b]pyridine in a suitable solvent, such as tetrahydrofuran, dioxane, or diethyl ether, at a temperature from about ambient to about 0° C., is reacted with a compound of structure M-C(O)-LG in the presence of a suitable base such as pyridine or triethylamine. This acylated product is then dissolved in a suitable solvent, such as tetrahydrofuran or diethyl ether, at a temperature from about ambient to about 0° C., and is treated with a suitable hydride reducing agent such as diborane or lithium aluminum hydride. The reaction is stirred from 1 to 24 hours and is then treated with an aqueous solution of sodium sulfate. The resultant suspension is filtered, and the filtrate concentrated under reduced pressure to provide the desired product.

Alternatively, a solution of a 5-aminopyrrolo[3,2-b] pyridine in a solvent suitable for the azeotropic removal of water, such as toluene, benzene or cyclohexane, is reacted at reflux with an appropriate aldehyde or ketone, such as formaldehyde, acetaldehyde, propanal, butanal or acetone, in the presence of 0.1–10% of a proton source such as p-toluenesulfonic acid. When the reaction is complete the volatiles are removed under reduced pressure and the residue redissolved in an alkanol such as methanol or ethanol. This solution is then subjected to hydrogenation conditions, or is treated with an appropriate hydride reducing agent, such as sodium borohydride or, preferably, sodium cyanoborohydride in the presence of an anhydrous acid such as hydrogen chloride. The product is isolated by a normal extractive workup.

Those compounds of the invention where X is —NHSO$_2$R$^2$ and —NHCOR$^6$ may be prepared in the alternative by the procedure described in Synthetic Scheme V where Y is —NHSO$_2$R$^2$ or —NHCOR$^6$, and R, R$^2$, and R$^6$ are as previously described.

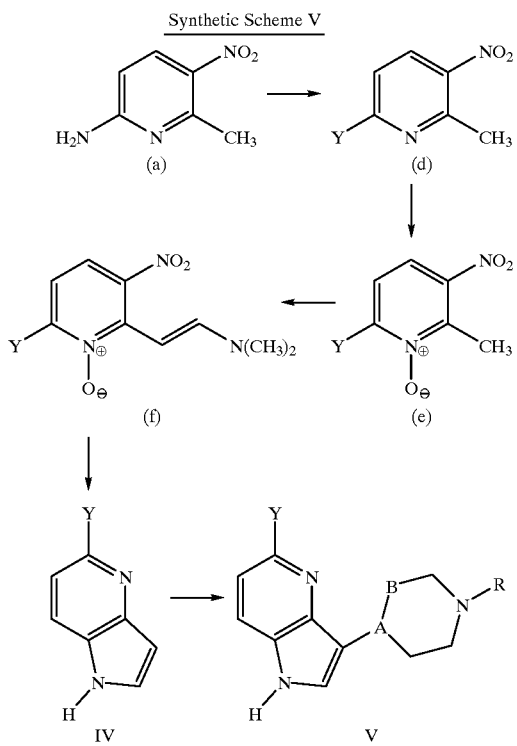

Synthetic Scheme V

The starting 2-methyl-3-nitro-6-aminopyridine (a) is either acylated with an appropriate carboxylic acid, anhydride, or acid halide, or reacted with an appropriate sulfonyl halide or anhydride under any of the conditions described for Synthetic Scheme I to provide the corresponding compound (d). This compound is subjected to standard amine oxidizing conditions, for example peracetic acid in acetic acid, to provide the corresponding N-oxide (e). This N-oxide is then subjected to the enamine formation, hydrogenation, and condensation sequence described for Synthetic Scheme II to provide the desired compounds of the invention. The skilled artisan will appreciate that this alternative route is applicable only to those $R^2$ and $R^6$ substituents which are stable to the various reaction conditions employed. The compounds of Formula IV are novel and represent a further embodiment of the present invention.

Certain compounds of the invention, while useful 5-$HT_{1F}$ agonists in their own right, are useful intermediates for the preparation of other compounds of the invention. Compounds of the invention where X is —NHC(O)$OR^5$ or —$NR^1$C(O)$R^6$, for example, may be subjected to either acid or base hydrolysis to provide the corresponding 5-amino-3-(piperidin-4-yl)pyrrolo[3,2-b]pyridines. This amine may then be subjected to any of the reaction conditions described for Synthetic Scheme I to prepare other compounds of the invention. Furthermore, the skilled artisan will appreciate that many of these reactions may be performed in any convenient order. For example, the 5-amino substituent may be modified prior or subsequent to the hydrogenation of the 1,2,3,6-tetrahydropyridin-4-yl moiety if convenient or desired. These variations are made apparent in the following Examples.

Preparation I 5-amino-3-(1-methyl-1,2,3,6-tetrahydropyridin-4-yl) pyrrolo[3,2-b]pyridine Nitration of 6-amino-2-picoline 110 gm (1.02 mole) molten 6-amino-2-picoline were added dropwise to 500 mL concentrated sulfuric acid which had been precooled to −15° C. at rate to maintain the temperature of the sulfuric acid solution under 20° C. The solution was then cooled to about −6° C. and then a solution of 49 mL 90% nitric acid (1.16 mole) in 49 mL sulfuric acid precooled to about 0° C. was added dropwise over about 30 minutes, maintaining the temperature at about 0° C. The reaction mixture was stirred at about 0° C. for one hour and was then allowed to warm to about 10° C. over an hour. The temperature of the reaction mixture was maintained at about 10° C. for one hour and was then allowed to warm to about 20° C. over an hour. The reaction mixture was maintained at about 20° C. for 2 hours. The reaction mixture was poured into 8 L of ice with vigorous stirring. The reaction mixture was then adjusted to pH ~9 by the addition of 1.5 L concentrated ammonium hydroxide, maintaining the temperature of the reaction mixture at about 24° C. by the addition of ice as needed. The resulting slurry was filtered and the solid washed several times with water. The solid was dried at 70° C. under vacuum for 3 days to provide 135.4 gm (87%) of a 2:1 mixture of 3-nitro-:5-nitro-6-amino-2-picoline.

Separation of Nitration Isomers by Sublimation 20 gm lots of the nitration mixture were sublimed twice under vacuum at 125° C. for 6 hours each. The 5-nitro isomer was sublimed as a bright yellow powder and discarded. The 3-nitro isomer which remained in the bottom of the sublimation apparatus was collected. A total of 121 gm were sublimed to provide 60.9 gm (75.5%) of the crude 3-nitro isomer. 58 gm of the crude 3-nitro isomer were slurried in 200 mL hot 95:5 ethanol:water. The mixture was cooled to room temperature and diluted with 200 mL of water. After two hours the precipitate was collected by filtration and rinsed several times with water. The solid was dried under vacuum at room temperature to provide 38 gm (65% based on 58 gm crude) 3-nitro-6-amino-2-picoline.

MS(m/e): 153 ($M^+$) Calculated for $C_6H_7N_3O_2$: Theory: C, 47.05; H, 4.61; N, 27.44. Found: C, 47.08; H, 4.53; N, 27.53.

Separation of Nitration Isomers by Recrystallization

A mixture of 20 gm of the nitration mixture and 800 mL toluene were heated at reflux for 15 minutes. The mixture was filtered at 95° C. and the mother liquors allowed to cool to room temperature. After 4 hours the crystalline solid was collected, washed with 100 mL toluene, and dried under reduced pressure at 50° C. for 16 hours to provide 13.7 gm (68%) 3-nitro-6-amino-2-picoline.

Preparation of 2-(2-dimethylaminoethen-1-yl)-5-nitro-6-(dimethylaminomethyleneimino)pyrrolo[3,2-b]pyridine (Intermediate III)

A mixture of 60 gm (0.39 mole) 3-nitro-6-amino-2-picoline in 260 mL dimethylformamide was treated with 260 mL (1.83 mole) 94% dimethylformamide dimethylacetal and the solution was heated at reflux for 48 hours. The reaction was concentrated under reduced pressure and the residual solid slurried with toluene. The toluene was evaporated under reduced pressure. This procedure was repeated 5 times. The final residue was slurried with 300 mL methyl tert-butyl ether and then filtered. This solid was washed 3 times with 300 mL methyl tert-butyl ether and the black solid was finally dried under reduced pressure to provide 90.6 gm (88%) of the desired compound.

MS(m/e): 263.1 ($M^+$) Calculated for $C_{12}H_{17}N_5O_2$: Theory: C, 54.74; H, 6.51; N, 26.60. Found: C, 54.84; H, 6.49; N, 26.79.

Preparation of 5-(dimethylaminomethyleneimino)pyrrolo[3,2-b]pyridine

A mixture of 90 gm (0.34 mole) Intermediate III and 6 gm 10% palladium on carbon in 650 mL ethanol was hydrogenated at 50 p.s.i. for 45 hours. The reaction mixture was filtered and the was concentrated under reduced pressure. The residual solid was slurried for 30 minutes with 70:30 methyl tert-butyl ether:ethyl acetate, filtered and rinsed with 3×300 mL 70:30 methyl tert-butyl ethyl:acetate. The solid was powdered and then slurried with 200 mL 70:30 methyl tert-butyl ether:ethyl acetate. The solid was filtered and dried under reduced pressure to provide 54.5 gm (85%) of the title compound as a yellow solid.

MS(m/e): 188.2 ($M^+$)

Condensation with 1-methyl-4-piperidone

A solution of 19.2 gm (0.10 mole) of 5-(dimethylaminomethyleneimino)pyrrolo[3,2-b]pyridine in 208 mL methanol was treated with 20 gm (0.30 mole) potassium hydroxide followed by 16.3 mL (0.13 mMol) 1-methyl-4-piperidone. The reaction mixture was heated under reflux for 24 hours and was then concentrated under reduced pressure. The residual solid was treated with 250 mL 9:1 ethyl acetate:tetrahydrofuran and 50 mL methanol. The solution was cooled to 0° C. and then 200 mL cold water were added. The phases were separated and the aqueous phase was extracted well with 9:1 ethyl acetate:tetrahydrofuran. All organic phases were combined, dried over sodium sulfate and concentrated under reduced pressure. The residual solid was slurried repeatedly with 475 mL cold water to remove black impurities. The remaining solid was dried under reduced pressure to provide 17 gm (74%) of the title compound as a yellow powder.

MS(m/e): 228.1 ($M^+$) Calculated for $C_{13}H_{16}N_4$: Theory: C, 68.39; H, 7.06; N, 24.54. Found: C, 68.13; H, 7.06; N, 24.38.

Preparation II 5-amino-3-(1-methylpiperidin-4-yl)pyrrolo[3,2-b] pyridine

A mixture of 21 gm (89.9 mMol) 5-amino-3-(1-methyl-1,2,3,6-tetrahydropyridin-4-yl)pyrrolo[3,2-b]pyridine and 10% palladium on carbon pre-wet with 30 mL ethanol in 180 mL methanol were hydrogenated at 65 p.s.i. for 3 days. The catalyst was removed by filtration and the filtrate concentrated under reduced pressure. The residual solid was slurried in 120 mL ethyl acetate, filtered, and washed 3×30 mL ethyl acetate. The remaining solid was dried under reduced pressure to provide 19 gm (92%) the title compound as a light brown solid.

MS(m/e): 230 (M$^+$) Calculated for $C_{13}H_{18}N_4$: Theory: C, 67.80; H, 7.88; N, 24.32. Found: C, 67.21; H, 7.79; N, 24.24.

Preparation III

Alternate Isolation of Intermediate III

A solution of 38.8 gm (0.25 mole) 3-nitro-6-amino-2-picoline in 172 mL dimethylformamide was treated with 172 mL dimethylformamide dimethylacetal and the mixture was heated at about 97° C. for 42 hours. The reaction mixture was then cooled to room temperature and was diluted with 650 mL isopropanol. The reaction mixture was allowed to stand for 18 hours at room temperature and was then cooled to 3–5° C. with stirring for an additional 2 hours. The slurry was filtered, the solid washed 2×75 mL isopropanol, and dried under reduced pressure at 45° C. for 16 hours to provide 58.9 gm (88%) of Intermediate III.

Preparation IV

Synthesis of Intermediate III from Mixture of Nitration Isomers

A mixture of 133 gm (0.86 mole) of a 2:1 mixture of 3-nitro:5-nitro-6-amino-2-picoline in 500 mL dimethylformamide was treated with 500 mL (3.5 mole) 94% dimethylformamide dimethylacetal and heated at reflux for 40 hours. After cooling to room temperature, the reaction mixture was divided in half and each half was poured into 10 L of water at 0° C. with vigorous stirring. After 10 minutes, the mixture was filtered and the solid was slurried/rinsed with 3×1 L of water. The solid was dried under vacuum at 65° C. for 2.5 days to provide 183 gm (81%) of the title compound as a red solid.

Preparation V

Alternate Synthesis of 5-amino-3-(1-methylpiperidin-4-yl)pyrrolo[3,2-b]pyridine
Preparation of 1-hydroxy-5-(dimethylaminomethylimino)pyrrolo[3,2-b]pyridine dihydrochloride A mixture of 23.4 gm (89 mMol) Intermediate III and 0.7 gm 10% palladium on carbon in 234 mL anhydrous methanol were treated with 140 mL 5.9 N ethanolic hydrogen chloride. The resulting mixture was hydrogenated for 1.5 hours under an initial hydrogen pressure of 30 p.s.i. The reaction mixture was diluted with 585 mL ethanol and was stirred at room tempreature for 1 hour at room temperature. The precipitate was filtered and rinsed with 50 mL ethanol. The solid was taken up in 1.1 L methanol, filtered, and then concentrated under reduced pressure. The residual solid was dried under reduced pressure to provide 20.5 gm (83%) of the desired compound (containing 5% 5-(dimethylaminomethylimino)pyrrolo[3,2-b]pyridine) as a yellow solid.
Preparation of 1-hydroxy-5-(dimethylaminomethylimino-3-(1-methyl-1,2,3,6-tetrahydropyridin-4-yl)pyrrolo[3,2-b]pyridine A mixture of 13.5 gm (48.7 mMol) 1-hydroxy-5-(dimethylaminomethylimino)pyrrolo[3,2-b]pyridine and 17.5 gm (155 mMol) 1-methyl-4-piperidone in 270 mL anhydrous ethanol was stirred until homogeneous. At this point 19.4 mL (109 mMol) 5.6 N dimethylamine in ethanol were added and the reaction mixture stirred at room temperature for 4 hours. The yellow precipitate was filtered, washed 2×27 mL ethanol, and dried under reduced pressure at 45° C. to provide 13.4 gm (92%) of the desired compound as a yellow solid.
Hydrogenation/hydrogenolysis A mixture of 0.28 gm (0.94 mMol) 1-hydroxy-5-(dimethylaminomethylimimo)-3-(1-methyl-1,2,3,6-tetrahydropyridin-4-yl)pyrrolo[3,2-b]pyridine and 0.10 gm 10% palladium on carbon in 20 mL methanol was hydrogenated for about 18 hours under an initial hydrogen pressure of 50 p.s.i. The reaction mixture was filtered and the filtrate concentrated under reduced pressure to provide 0.21 gm (96%) of the title compound.

Preparation VI 5-amino-3-(1-tert-butoxycarbonyl-1,2,3,6-tetrahydropyridin-4-yl)pyrrolo[3,2-b]pyridine Beginning with 0.75 gm (3.98 mMol) 5-substituted pyrrolo[3,2-b]pyridine (c) and 1.6 gm (7.96 mMol) 1-tert-butoxycarbonyl-4-piperidone, 1.07 gm (86%) of the title compound were prepared as a yellow foam essentially by the procedure of Preparation I.

MS(m/e): 314(M$^+$) Calculated for $C_{17}H_{22}N_4O_2$: Theory: C, 64.95; H, 7.05; N, 17.82. Found: C, 64.73; H, 7.09; N, 17.92.

Preparation VII 5-amino-3-(1-tert-butoxycarbonylpiperidin-4-yl)pyrrolo[3,2-b]pyridine Beginning with 1.07 gm (3.4 mMol) 5-amino-3-(1-tert-butoxycarbonyl-1,2,3,6-tetrahydropyridin-4-yl)pyrrolo[3,2-b]pyridine, 0.89 gm (83%) of the title compound were prepared essentially by the procedure of Preparation II.

MS(m/e): 316(M$^+$)

EXAMPLE 1

5-(N-acetylamino)-3-(1-methyl-1,2,3,6-tetrahydropyridin-4-yl)pyrrolo[3,2-b]pyridine
Preparation of Acetamide (d), $R^6=CH_3$ A mixture of 21.8 gm (142.4 mMol) 2-methyl-3-nitro-6-aminopyridine and 28 mL (298.9 mMol) acetic anhydride was heated at 120° C. for 1.5 hours. The reaction mixture was then concentrated under reduced pressure and the residue slurried in water for 18 hours. The slurry was filtered and the solid dried under vacuum at 50° C. for 2 hours. The remaining solid was recrystallized from methanol to provide 23.5 gm (85%) of the desired compound as brown needles in two crops.
Preparation of N-oxide (e), $R^6=CH_3$ A solution of 14 mL (66.2 mMol) peracetic acid (4.8 M) in aqueous acetic acid was added dropwise to a suspension of 11.8 gm (60.2 mMol) of the acetamide (e) in 30 mL acetic acid. The mixture was stirred at 25° C. for 2 hours and was then gradually warmed to 60° C. and maintained at that temperature for 18 hours. The reaction mixture was concentrated under reduced pressure and the residue suspended in 200 mL water. The mixture was cooled and the solid collected by filtration and then dried under vacuum to provide 11.07 gm (87%)of the desired compound.
Preparation of enamine (f), $R^6=CH_3$ A mixture of 11.1 gm (52.6 mMol) N-oxide (e) and 7.7 mL (57.8 mMol) dimethylformamide dimethylacetal in 25 mL dimethylformamide was heated at 90° C. for 4 hours. Volatiles were removed under reduced pressure and residual dimethylformamide removed by azeotropic distillation with toluene. The residue was subjected to silica gel chromatography, eluting with a gradient of dichloromethane (1–5% methanol). Fractions containing product were combined and concentrated under reduced pressure to provide 9.15 gm (65%) of the desired compound as a red solid.

Preparation of 5-(N-acetylamino)pyrrolo[3,2-b]pyridine

A mixture of 9.3 gm (34.9 mMol) of enamine (f) and 4 gm palladium on carbon in 1 L tetrahydrofuran:ethanol (1:1) was hydrogenated at 60° C. under balloon pressure for 44 hours. At this point the reaction was filtered and the filtrated concentrated under reduced pressure. The residue was redissolved in 700 mL tetrahydrofuran:ethanol (1:1), 4 gm palladium on carbon were added, and the mixture was again hydrogenated at 60° C. under balloon pressure. The residue was subjected to silica gel chromatography, eluting with a gradient of ethyl acetate (5–20%) methanol). Fractions containing product were combined and concentrated under reduced pressure to provide 4.99 gm (81%) of the desired product as an ivory solid.

Condensation with 1-methyl-4-piperidone

A solution of 0.477 gm (2.7 mMol) of the 5-(N-acetylamino)pyrrolo[3,2-b]pyridine, 0.54 mg (9.5 mMol) potassium hydroxide, and 0.43 mL (3.5 mMol) 1-methyl-4-piperidone in 15 mL methanol was heated at reflux for 18 hours. The reaction mixture was then concentrated under reduced pressure and the residue dissolved in pyridine. To this solution was added 0.20 mL (2.2 mMol) acetic anhydride and the resultant mixture stirred for 1 hour. This reaction mixture was concentrated under reduced pressure. The residue was subjected to silica gel chromatography, eluting with a gradient of ethyl acetate (2–40%) methanol). Fractions containing product were combined and concentrated under reduced pressure to provide 0.43 gm (59%) 5-(N-acetylamino)-3-(1-methyl-1,2,3,6-tetrahydropyridin-4-yl)pyrrolo[3,2-b]pyridine as an ivory foam. A portion was recrystallized from methanol/ethyl acetate to provide an analytical sample.

m.p.=191.5–193.0° C. (dec.)

MS(m/e): 270 ($M^+$)

EXAMPLE 2

5-N-acetylamino)-3-(1-methylpiperidin-4-yl)pyrrolo[3,2-b]pyridine

A mixture of 0.30 gm (1.1 mMol) 5-(N-acetylamino)-3-(1-methyl-1,2,3,6-tetrahydropyridin-4-yl)pyrrolo[3,2-b]pyridine and 0.05 gm 10% palladium of carbon in 15 mL ethanol was hydrogenated at room temperature for 18 hours at an initial hydrogen pressure of 50 p.s.e. The reaction mixture was filtered and the filtrate concentrated under reduced pressure. The residue was subjected to silica gel chromatography, eluting with ethyl acetate containing 20% methanol and 1% ammonium hydroxide. Fractions containing product were combined and concentrated under reduced pressure to provide the title compound.

m.p.=196–197.2° C. (dec.)

MS(m/e): 272 ($M^+$)

EXAMPLE 3

Alternate preparation of 5-amino-3-(1-methylpiperidin-4-yl)pyrrolo[3,2-b]pyridine A mixture of 2.5 gm (9.2 mMol) 5-(N-acetylamino)-3-(1-methylpiperidin-4-yl)pyrrolo[3,2-b]pyridine in 40 mL 2N hydrochloric acid was heated at reflux for 1 hour. The reaction mixture was cooled to room temperature, concentrated under reduced pressure, basified (pH~11) with 2N aqueous sodium hydroxide, concentrated under reduced pressure, and extracted well with 3:1 chloroform:isopropanol. The organic extracts were combined, dried over magnesium sulfate and concentrated under reduced pressure to provide 1.98 gm (93%) of the title compound as a brown solid.

MS(m/e): 230 ($M^+$)

Calculated for $C_{13}H_{18}N_4$: Theory: C, 67.80; H, 7.88; N, 24.33. Found: C, 67.62; H, 7.57; N, 24.54.

EXAMPLE 4

5-(N-[cyclopropanecarbonyl]amino)-3-(1-methylpiperidin-4-yl)pyrrolo[3,2-b]pyridine A solution of 0.300 gm (1.30 mMol) 5-amino-3-(1-methylpiperidin-4-yl)pyrrolo[3,2-b]pyridine in 40 mL pyridine was heated to 50° C. To this solution was added 0.13 mL (1.43 mMol) cyclopropanecarbonyl chloride and the reaction mixture was stirred for 1.5 hours. An additional 0.10 mL of cyclopropanecarbonyl chloride were added and the reaction mixture was stirred for an additional hour. The reaction mixture was treated with 1.0 mL of water and was then concentrated under reduced pressure. The residue was diluted with 3:1 chloroform: isopropanol and the solution washed sequentially with water, dilute aqueous sodium hydroxide, and saturated aqueous sodium chloride. The organic phase was then dried over sodium sulfate and concentrated under reduced pressure. The residue was subjected to radial chromatography (silica gel, 1 mm), eluting with a gradient of dichloromethane (5–10% methanol) containing 1% ammonium hydroxide. Fractions containing product were combined and concentrated under reduced pressure. The residue was recrystallized from ethanol/water to provide 0.22 gm (55.9%) of the title compound as a crystalline solid.

MS(m/e): 298 ($M^+$)

Calculated for $C_1H_{22}N_4O$-0.1 $H_2O$: Theory: C, 68.01; H, 7.45; N, 18.66. Found: C, 68.08; H, 7.52; N, 18.42.

EXAMPLE 5

5-(N-[cyclobutanecarbonyl]amino)-3-(1-methylpiperidin-4-yl)pyrrolo[3,2-b]pyridine Beginning with 0.25 gm (1.08 mMol) 5-amino-3-(1-methylpiperidin-4-yl)pyrrolo[3,2-b]pyridine and 0.136 gm (1.19 mMol) cyclobutanecarbonyl chloride, 0.17 gm (50.8%) of the title compound were prepared essentially by the procedure described in Example 4.

m.p.=104° C.

MS/(m/e): 312 ($M^+$)

Calculated for $C_{18}H_{24}N_4O$: Theory: C, 69.20; H, 7.74; N, 17.93. Found: C, 69.38; H, 7.85; N, 17.85

EXAMPLE 6

5-(N-[cyclopentanecarbonyl]amino)-3-(1-methylpiperidin-4-yl)pyrrolo[3,2-b]pyridine Beginning with 0.080 gm (0.348 mMol) 5-amino-3-(1-methylpiperidin-4-yl)pyrrolo[3,2-b]pyridine and 0.093 mL (0.766 mMol) cyclopentanecarbonyl chloride, 0.095 gm (84%) of the title compound was recovered as an amorphous solid essentially by the procedure described in Example 4.

m.p.=119.3–120.9° C.

MS(m/e): 326 ($M^+$)

EXAMPLE 7

5-(N-[cyclohexanecarbonyl]amino)-3-(1-methylpiperidin-4-yl)pyrrolo[3,2-b]pyridine A solution of 0.010 gm (0.044 mMol) 5-amino-3-(1-methylpiperidin-4-yl)pyrrolo[3,2-b]pyridine in 1.0 mL pyridine was heated to 50 °C. To this solution were then added 0.0064 mL (0.048 mMol) cyclohexanecarbonyl chloride and the reaction mixture stirred for 1 hour. The reaction mixture is concentrated under reduced pressure and a solution of the residue in methanol passed over a VARIAN BOND ELUT SCX™ (Varian, Harbor City, Calif., U.S.A.) ion exchange column which had been preactivated with 10% acetic acid in methanol. The column was washed thoroughly with methanol and then the desired product eluted with 2M ammonia in methanol. Fractions containing product were combined and concentrated under reduced pressure to provide 0.013 gm (87.2%) of the title compound.

MS(m/e): 341 (M$^+$)

EXAMPLE 8

5-(N-[propionyl]amino)-3-(1-methylpiperidin-4-yl)pyrrolo[3,2-b]pyridine

Beginning with 2.0 gm (8.7 mMol) 5-amino-3-(1-methylpiperidin-4-yl)pyrrolo[3,2-b]pyridine and 0.91 mL (10.4 mMol) propionyl chloride, 2.58 gm of the title compound were prepared as a crude brown foam essentially by the procedure described in Example 4. The residue was subjected to flash silica gel chromatography, eluting with dichloromethane containing 10% methanol and 1% ammonium hydroxide. Fractions containing product were combined and concentrated under reduced pressure. This residue was crystallized from ethanol:water to provide 1.74 gm (70%) of the title compound in two crops.

m.p.=98.9–101° C.

MS(m/e): 286 (M$^+$)

Calculated for $C_{16}H_{22}N_4O$: Theory: C, 67.11; H, 7.74; N, 19.56. Found: C, 66.97; H, 7.59; N, 19.47.

EXAMPLE 9

5-(N-[butyryl]amino)-3-(1-methylpiperidin-4-yl)pyrrolo[3,2-b]pyridine

Beginning with 0.30 gm (1.3 mMol) 5-amino-3-(1-methylpiperidin-4-yl)pyrrolo[3,2-b]pyridine and 0.165 mL (1.56 mMol) butyryl chloride, 0.22 gm of the title compound were prepared as an ivory foam essentially by the procedure described in Example 4. This residue was crystallized from ethanol:water to provide material for analysis.

MS(m/e): 300 (M$^+$)

Calculated for $C_{17}H_{24}N_4O$: Theory: C, 67.97; H, 8.05; N, 18.65. Found: C, 67.38; H, 7.79; N, 18.32.

EXAMPLE 10

5-(N-[pentanoyl]amino)-3-(1-methylpiperidin-4-yl)pyrrolo[3,2-b]pyridine

Beginning with 0.01 gm (0.044 mMol) 5-amino-3-(1-methylpiperidin-4-yl)pyrrolo[3,2-b]pyridine and 0.0066 mL (0.048 mMol) pentanoyl chloride, 0.103 gm (91%) of the title compound were prepared essentially by the procedure described in Example 7.

MS(m/e): 315 (M+1)

EXAMPLE 11

5-(N-[hexanoyl]amino)-3-(1-methylpiperidin-4-yl) pyrrolo[3,2-b]pyridine

Beginning with 0.01 gm (0.004 mMol) 5-amino-3-(1-methylpiperidin-4-yl)pyrrolo[3,2-b]pyridine and 0.0077 mL (0.048 mMol) hexanoyl chloride, 0.012 gm (84%) of the title compound were prepared essentially by the procedure described in Example 7.

MS(m/e):329 (M+1)

EXAMPLE 12

5-(N-[octanoyl]amino)-3-(1-methylpiperidin-4-yl)pyrrolo[3,2-b]pyridine

Beginning with 0.01 gm (0.044 mMol) 5-amino-3-(1-methylpiperidin-4-yl)pyrrolo[3,2-b]pyridine and 0.10 mL (0.057 mMol) octanoyl chloride, 0.013 gm (83%) of the title compound were prepared essentially by the procedure described in Example 7.

MS(m/e): 357 (M+1)

EXAMPLE 13

5-(N-[2-methylpropanoyl]amino)-3-(1-methylpiperidin-4-yl)pyrrolo[3,2-b]pyridine

Beginning with 0.35 gm (0.154 mMol) 5-amino-3-(1-methylpiperidin-4-yl)pyrrolo[3,2-b]pyridine and 0.20 mL (0.193 mMol) 2-methylpropanoyl chloride, 0.35 gm (75%) of the title compound were prepared essentially by the procedure described in Example 8.

MS(m/e): 300 (M$^+$)

EXAMPLE 14

5-(N-[3-methylbutanoyl]amino)-3-(1-methylpiperidin-4-yl)pyrrolo[3,2-b]pyridine

Beginning with 0.010 gm (0.044 mMol) 5-amino-3-(1-methylpiperidin-4-yl)pyrrolo[3,2-b]pyridine and 0.048 mMol 3-methylbutanoyl chloride, 0.008 gm (60%) of the title compound were prepared essentially by the procedure described in Example 7.

MS(m/e): 315 (M+1)

EXAMPLE 15

5-(N-[2,2-dimethylpropanoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.067 mL (0.048 mMol) 2,2-dimethylpropanoyl chloride, 0.067 gm (48%) of the title compound were prepared essentially by the procedure described in Example 7.

MS(m/e): 315 (M$^+$)

EXAMPLE 16

5-(N-[benzoyl]amino)-3-(1-methylpiperidin-4-yl)pyrrolo[3,2-b]pyridine

To a solution of 0.100 gm (0.43 mMol) 5-amino-3-(1-methylpiperidin-4-yl)pyrrolo[3,2-b]pyridine in 3 mL 50% aqueous tetrahydrofuran were added 0.43 mL (0.86 mMol) benzoyl chloride and the resulting mixture was stirred at room temperature. After about 4 hours the reaction mixture was partitioned between dichloromethane and 2N sodium hydroxide. The phases were separated and the aqueous phase extracted well with dichloromethane. The organic phases were combined, dried over sodium sulfate and concentrated under reduced pressure. The residue was subjected to silica gel chromatography, eluting with a gradient of dichloromethane (2–10% methanol) containing 1% ammonium hydroxide. Fractions containing product were combined and concentrated under reduced pressure to provide 0.095 gm (66%) of the title compound. A portion was recrystallized from ethanol/water to provide an analytical sample.

m.p.=110.7–113.6° C.

MS(m/e): 334 (M$^+$)

Calculated for $C_{20}H_{22}N_4O$: Theory: C, 71.83; H, 6.63; N, 16.75. Found: C, 72.05; H, 6.47; N, 16.66.

EXAMPLE 17
5-(N-[2-fluorobenzoyl]amino)-3-(1-methylpiperidin-4-yl)pyrrolo[3,2-b]pyridine Beginning with 0.085 gm (0.369 mMol) 5-amino-3-(1-methylpiperidin-4-yl)pyrrolo[3,2-b]pyridine and 0.093 mL (0.776 mMol) 2-fluorobenzoyl chloride, 0.106 gm (82%) of the title compound was recovered as a crystalline solid by the procedure described in Example 16.
m.p.=125–126° C.
MS(m/e): 352 (M$^+$)
Calculated for $C_{20}H_{21}N_4OF$: Theory: C, 68.16; H, 6.01; N, 15.90. Found: C, 68.44; H, 6.07; N, 15.97.

EXAMPLE 18
5-(N-[3-fluorobenzoyl]amino)-3-(1-methylpiperidin-4-yl)pyrrolo[3,2-b]pyridine Beginning with 0.085 gm (0.369 mMol) 5-amino-3-(1-methylpiperidin-4-yl)pyrrolo[3,2-b]pyridine and 0.093 mL (0.776 mMol) 3-fluorobenzoyl chloride, 0.100 gm (77.5%) of the title compound was recovered as a crystalline solid by the procedure described in Example 16.
m.p.=129–130° C.
MS(m/e): 352 (M$^+$)

EXAMPLE 19
5-(N-[4-fluorobenzoyl]amino)-3-(1-methylpiperidin-4-yl)pyrrolo[3,2-b]pyridine A solution of 1.00 gm (4.3 mMol) 5-amino-3-(1-methylpiperidin-4-yl)pyrrolo[3,2-b]pyridine in 85 mL pyridine was heated to 55° C. To this solution were added 0.57 mL (4.8 mMol) 4-fluorobenzoyl chloride and the resulting mixture was stirred for 30 minutes at which time an additional 0.10 mL 4-fluorobenzoyl chloride were added. After stirring for an additional 10 minutes the reaction mixture was concentrated under reduced pressure. The residue was treated with 50 mL cold 1N sodium hydroxide followed by 100 mL dichloromethane. The phases were separated and the aqueous phase was extracted 2×50 mL dichloromethane followed by 3×50 mL 3:1 chloroform:isopropanol. The organic phases were combined, washed with saturated aqueous sodium chloride, dried over magnesium sulfate, and concentrated under reduced pressure. The residue was subjected to radial chromatography (4 mm silica gel plate) eluting with dichloromethane containing 10–20% methanol and 1% ammonium hydroxide. Fractions containing product were combined and concentrated under reduced pressure. The residue was crystallized from aqueous ethanol to provide 1.32 gm (87%) of the title compound as ivory crystals.
MS(m/e): 352 (M$^+$)
Calculated for $C_{20}H_{21}N_4OF$: Theory: C, 68.16; H, 6.01; N, 15.90. Found: C, 68.01; H, 5.96; N, 15.88.

EXAMPLE 20
5-(N-[3-chlorobenzoyl]amino)-3-(1-methylpiperidin-4-yl)pyrrolo[3,2-b]pyridine Beginning with 0.085 gm (0.369 mMol) 5-amino-3-(1-methylpiperidin-4-yl)pyrrolo[3,2-b]pyridine and 0.099 mL (0.776 mMol) 3-chlorobenzoyl chloride, 0.109 gm (80.1%) of the title compound was recovered as a crystalline solid by the procedure described in Example 16.
m.p.=110–111° C.
MS(m/e): 368 (M$^+$)

EXAMPLE 21
5-(N-[4-bromobenzoyl]amino)-3-(1-methylpiperidin-4-yl)pyrrolo[3,2-b]pyridine Beginning with 0.090 gm (0.39 mMol) 5-amino-3-(1-methylpiperidin-4-yl)pyrrolo[3,2-b]pyridine and 0.128 gm (0.59 mMol) 4-bromobenzoyl chloride, 0.053 gm (23%) of the title compound was recovered as a crystalline solid by the procedure described in Example 4.
Calculated for $C_{20}H_{21}N_4OBr$: Theory: C, 58.12; H, 5.12; N, 13.56. Found: C, 58.41; H, 5.04; N, 13.74

EXAMPLE 22
5-(N-[4-iodobenzoyl]amino)-3-(1-methylpiperidin-4-yl)pyrrolo[3,2-b]pyridine Beginning with 0.090 gm (0.39 mMol) 5-amino-3-(1-methylpiperidin-4-yl)pyrrolo[3,2-b]pyridine and 0.157 gm (0.59 mMol) 4-iodobenzoyl chloride, 0.035 gm (19%) of the title compound was recovered as a crystalline solid by the procedure described in Example 4.
Calculated for $C_{20}H_{21}N_4OI$: Theory: C, 52.19; H, 4.60; N, 12.17. Found: C, 52.39; H, 4.79; N, 12.35.

EXAMPLE 23
5-(N-[4-cyanobenzoyl]amino)-3-(1-methylpiperidin-4-yl)pyrrolo[3,2-b]pyridine Beginning with 0.100 gm (0.43 mMol) 5-amino-3-(1-methylpiperidin-4-yl)pyrrolo[3,2-b]pyridine and 0.093 gm (0.56 mMol) 4-cyanobenzoyl chloride, 0.068 gm (44%) of the title compound was recovered as a crystalline solid by the procedure described in Example 4.
m.p.=129.2–133.6° C.
MS(m/e): 359 (M$^+$)
Calculated for $C_{21}H_{21}N_5O$: Theory: C, 70.18; H, 5.89; N, 19.48. Found: C, 70.43; H, 5.85; N, 19.61.

EXAMPLE 24
5-(N-[4-nitrobenzoyl]amino)-3-(1-methylpiperidin-4-yl)pyrrolo[3,2-b]pyridine Beginning with 0.100 gm (0.43 mMol) 5-amino-3-(1-methylpiperidin-4-yl)pyrrolo[3,2-b]pyridine and 0.103 gm (0.56 mMol) 4-nitrobenzoyl chloride, 0.058 gm (36%) of the title compound was recovered as a crystalline solid by the procedure described in Example 4.
m.p.=235.8–238.0° C. (dec.)
MS(m/e): 379 (M$^+$)
Calculated for $C_{20}H_{25}N_5O_3$: Theory: C, 63.31; H, 5.58; N, 18.46. Found: C, 63.12; H, 5.83; N, 18.61.

EXAMPLE 25
5-(N-[2,4-dichlorobenzoyl]amino)-3-(1-methylpiperidin-4-yl)pyrrolo[3,2-b]pyridine Beginning with 0.085 gm (0.369 mMol) 5-amino-3-(1-methylpiperidin-4-yl)pyrrolo[3,2-b]pyridine and 0.108 mL (0.776 mMol) 2,4-dichlorobenzoyl chloride, 0.108 gm (72.7%) of the title compound was recovered as an amorphous solid by the procedure described in Example 16.
m.p.=151–152° C.
MS(m/e): 402 (M$^+$)
Calculated for $C_{20}H_{20}N_4OCl_2$: Theory: C, 59.56; H, 5.00; N, 13.89. Found: C, 59.69; H, 5.10; N, 14.15.

EXAMPLE 26
5-(N-[3-pyridinecarbonyl]amino)-3-(1-methylpiperidin-4-yl)pyrrolo[3,2-b]pyridine Beginning with 0.078 gm (0.339 mMol) 5-amino-3-(1-methylpiperidin-4-yl)pyrrolo[3,2-b]pyridine and 0.127 gm (0.712 mMol) 3-pyridinecarbonyl chloride hydrochloride, 0.106 gm (82%) of the title compound was recovered as a crystalline solid by the procedure described in Example 16.
m.p.=136–137° C.
MS(m/e): 335 (M$^+$)

EXAMPLE 27
5-(N-[4-pyridinecarbonyl]amino)-3-(1-methylpiperidin-4-yl)pyrrolo[3,2-b]pyridine Beginning with 0.065 gm (0.282 mMol) 5-amino-3-(1-methylpiperidin-4-yl)pyrrolo[3,2-b]pyridine and 0.106 gm (0.593 mMol) 4-pyridinecarbonyl chloride hydrochloride, 0.053 gm (56%) of the title compound was recovered as an amorphous solid by the procedure described in Example 16.
m.p.=126.5–128.4° C.
MS(m/e): 335 ($M^+$)

EXAMPLE 28
5-(N-[2-furoyl]amino)-3-(1-methylpiperidin-4-yl)pyrrolo[3,2-b]pyridine Beginning with 0.200 gm (0.87 mMol) 5-amino-3-(1-methylpiperidin-4-yl)pyrrolo[3,2-b]pyridine and 0.171 mL (1.74 mMol) 2-furoyl chloride, 0.090 gm (32%) of the title compound was recovered as a crystalline solid from methanol/ethyl acetate by the procedure described in Example 16.
m.p.=251.0–253.3° C. (dec.)
MS(m/e): 324 ($M^+$)
Calculated for $C_{18}H_{20}N_4O_2$: Theory: C, 66.65; H, 6.21; N, 17.27. Found: C, 66.88; H, 6.34; N, 17.45.

EXAMPLE 29
5-(N-[2-thiophenecarbonyl]amino)-3-(1-methylpiperidin-4-yl)pyrrolo[3,2-b]pyridine Beginning with 0.100 gm (0.43 mMol) 5-amino-3-(1-methylpiperidin-4-yl)pyrrolo[3,2-b]pyridine and 0.056 mL (0.52 mMol) 2-thiophenecarbonyl chloride, 0.052 gm (34%) of the title compound was recovered as a crystalline solid by the procedure described in Example 4.
MS(m/e): 340 ($M^+$)
Calculated for $C_{18}H_{20}N_4OS$: Theory: C, 63.50; H, 5.92; N, 16.46. Found: C, 63.21; H, 6.10; N, 16.39.

EXAMPLE 30
5-(N-[2-chlorobenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.067 mL (0.53 mMol) 2-chlorobenzoyl chloride, 0.015 gm (91%) of the title compound were prepared essentially by the procedure described in Example 7.
MS(m/e): 369 ($M^+$)

EXAMPLE 31
5-(N-[2-bromobenzoyl]amino)-3-(1-methylpiperidin-4-yl)pyrrolo[3,2-b]pyridine Beginning with 0.015 gm (0.065 mMol) 5-amino-3-(1-methylpiperidin-4-yl)pyrrolo[3,2-b]pyridine and 0.0099 mL (0.072 mMol) 2-bromobenzoyl chloride, 0.026 gm (96%) of the title compound were prepared essentially by the procedure described in Example 7.
MS(m/e): 412 ($M^+$)

EXAMPLE 32
5-(N-[3-bromobenzoyl]amino)-3-(1-methylpiperidin-4-yl)pyrrolo[3,2-b]pyridine Beginning with 0.015 gm (0.065 mMol) 5-amino-3-(1-methylpiperidin-4-yl)pyrrolo[3,2-b]pyridine and 0.0095 mL (0.072 mMol) 3-bromobenzoyl chloride, 0.024 gm (90%) of the title compound were prepared essentially by the procedure described in Example 7.
MS(m/e): 412 ($M^+$)

EXAMPLE 33
5-(N-[3-cyanobenzoyl]amino)-3-(1-methylpiperidin-4-yl)pyrrolo[3,2-b]pyridine Beginning with 0.015 gm (0.065 mMol) 5-amino-3-(1-methylpiperidin-4-yl)pyrrolo[3,2-b]pyridine and 0.012 mL (0.072 mMol) 3-cyanobenzoyl chloride, 0.021 gm (92%) of the title compound were prepared essentially by the procedure described in Example 7.
MS(m/e): 359 ($M^+$)

EXAMPLE 34
5-(N-[2-methylbenzoyl]amino)-3-(1-methylpiperidin-4-yl)pyrrolo[3,2-b]pyridine Beginning with 0.015 gm (0.065 mMol) 5-amino-3-(1-methylpiperidin-4-yl)pyrrolo[3,2-b]pyridine and 0.0094 mL (0.072 mMol) 2-methylbenzoyl chloride, 0.023 gm (100%) of the title compound were prepared essentially by the procedure described in Example 7.
MS(m/e): 348 ($M^+$)

EXAMPLE 35
5-(N-[3-methylbenzoyl]amino)-3-(1-methylpiperidin-4-yl)pyrrolo[3,2-b]pyridine Beginning with 0.015 gm (0.065 mMol) 5-amino-3-(1-methylpiperidin-4-yl)pyrrolo[3,2-b]pyridine and 0.0095 mL (0.072 mMol) 3-methylbenzoyl chloride, 0.022 gm (99%) of the title compound were prepared essentially by the procedure described in Example 7.
MS(m/e): 348 ($M^+$)

EXAMPLE 36
5-(N-[4-methylbenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.007 mL (0.058 mMol) 4-methylbenzoyl chloride, 0.010 gm (66%) of the title compound were prepared essentially by the procedure described in Example 7.
MS(m/e): 349 ($M^+$)

EXAMPLE 37
5-(N-[4-tert-butylbenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.011 mL (0.057 mMol) 4-tert-butylbenzoyl chloride, 0.013 gm (76%) of the title compound were prepared essentially by the procedure described in Example 7.
MS(m/e): 391 ($M^+$)

EXAMPLE 38
5-(N-[2-trifluoromethylbenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.008 mL (0.053 mMol) 2-trifluoromethylbenzoyl chloride, 0.017 gm (96%) of the title compound were prepared essentially by the procedure described in Example 7.
MS(m/e): 403 ($M^+$)

EXAMPLE 39
5-(N-[4-trifluoromethylbenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.008 mL (0.058 mMol) 4-trifluoromethylbenzoyl chloride, 0.013 gm (73%) of the title compound were prepared essentially by the procedure described in Example 7.
MS(m/e): 403 ($M^+$)

EXAMPLE 40
5-(N-[2-methoxybenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.008 mL (0.058 mMol) 2-methoxybenzoyl chloride, 0.006 gm (39%) of the title compound were prepared essentially by the procedure described in Example 7.
MS(m/e): 365 (M+1)

EXAMPLE 41
5-(N-[3-methoxybenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.004 mL (0.058 mMol) 3-methoxybenzoyl chloride, 0.016 gm (98%) of the title compound were prepared essentially by the procedure described in Example 7.
MS(m/e): 365 (M+1)

EXAMPLE 42
5-(N-[4-methoxybenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.058 mMol 4-methoxybenzoyl chloride, the title compound was prepared essentially by the procedure described in Example 7.
MS(m/e): 364 (M$^+$)

EXAMPLE 43
5-(N-[4-trifluoromethoxybenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.012 mL (0.053 mMol) 4-trifluoromethoxybenzoyl chloride, the title compound were prepared essentially by the procedure described in Example 7.
MS(m/e): 419 (M+1)

EXAMPLE 44
5-(N-[2-nitrobenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.007 mL (0.048 mMol) 2-nitrobenzoyl chloride, 0.015 gm (92%) of the title compound was prepared essentially by the procedure described in Example 7.
MS(m/e): 380 (M+1)

EXAMPLE 45
5-(N-[3-nitrobenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.048 mMol 3-nitrobenzoyl chloride, the title compound was prepared essentially by the procedure described in Example 7.
MS(m/e): 380 (M+1)

EXAMPLE 46
5-(N-[3,4-difluorobenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.007 mL (0.055 mMol) 3,4-difluorobenzoyl chloride, 0.014 gm (80%) of the title compound was prepared essentially by the procedure described in Example 7.
MS(m/e): 371 (M+1)

EXAMPLE 47
5-(N-[2,4-difluorobenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.006 mL (0.053 mMol) 2,4-difluorobenzoyl chloride, 0.012 gm (77%) of the title compound was prepared essentially by the procedure described in Example 7.
MS(m/e): 371 (M+1)

EXAMPLE 48
5-(N-[2,6-difluorobenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.007 mL (0.053 mMol) 2,6-difluorobenzoyl chloride, the title compound was prepared essentially by the procedure described in Example 7.
MS(m/e): 371 (M+1)

EXAMPLE 49
5-(N-[2-fluoro-4-trifluoromethylbenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.012 mL (0.053 mMol) 2-fluoro-4-trifluoromethylbenzoyl chloride, the title compound was prepared essentially by the procedure described in Example 7.
MS(m/e): 421 (M+1)

EXAMPLE 50
5-(N-[2,4,5-trifluorobenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.007 mL (0.055 mMol) 2,4,5-trifluorobenzoyl chloride, 0.015 gm (86%) of the title compound was prepared essentially by the procedure described in Example 7.
MS(m/e): 389 (M+1)

EXAMPLE 51
5-(N-[2,3,4,5,6-pentafluorobenzoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.008 mL (0.053 mMol) 2,3,4,5,6-pentafluorobenzoyl chloride, 0.016 gm (84%) of the title compound was prepared essentially by the procedure described in Example 7.
MS(m/e): 425 (M+1)

EXAMPLE 52
5-(N-[3-furoyl]amino)-3-(1-methylpiperidin-4-yl)pyrrolo[3,2-b]pyridine Beginning with 1.0 gm (4.3 mMol) 5-amino-3-(1-methylpiperidin-4-yl)pyrrolo[3,2-b]pyridine and 0.68 gm (5.2 mMol) 3-furoyl chloride, 0.85 gm (61%) of the title compound were prepared as an ivory crystalline solid essentially by procedure described in Example 4.
m.p.=105.3–108.4° C.
MS(m/e): 324 (M$^+$)

EXAMPLE 53
5-(N-[5-nitro-2-furoyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.0093 mL (0.053 mMol) 5-nitro-2-furoyl chloride, 0.010 gm (64%) of the title compound was prepared essentially by the procedure described in Example 7.
MS(m/e): 370 (M+1)

EXAMPLE 54

5-(N-[3-thiophenecarbonyl]amino)-3-(1-methylpiperidin-4-yl)pyrrolo[3,2-b]pyridine Beginning with 1.5 gm (6.5 mMol) 5-amino-3-(1-methylpiperidin-4-yl)pyrrolo[3,2-b]pyridine and 1.2 gm (7.8 mMol) 3-thiophenecarbonyl chloride, 1.42 gm (64%) of the title compound were prepared essentially by the procedure described in Example 4.

m.p.=123.2–126.8° C.

MS(m/e): 340 (M$^+$)

Calculated for $C_{18}H_{20}N_4OS$: Theory: C, 63.50; H, 5.92; N, 16.46. Found: C, 63.61; H, 5.94; N, 16.33.

EXAMPLE 55

5-(N-[5-fluoro-2-thiophenecarbonyl]amino)-3-(1-methylpiperidin-4-yl)pyrrolo[3,2-b]pyridine Beginning with 0.414 gm (1.8 mMol) 5-amino-3-(1-methylpiperidin-4-yl)pyrrolo[3,2-b]pyridine and 2.73 mMol 5-fluoro-2-thiophenecarbonyl chloride, 0.11 gm (17%) of the title compound were prepared essentially by the procedure described in Example 4.

m.p.=244–245° C.

MS(m/e): 358 (M$^+$)

Calculated for $C_{18}H_{19}FN_4OS$: Theory: C, 60.32; H, 5.34; N, 15.63. Found: C, 60.59; H, 5.34; N, 15.72.

EXAMPLE 56

5-(N-[3-chloro-2-thiophenecarbonyl]amino)-3-(1-methylpiperidin-4-yl)pyrrolo[3,2-b]pyridine Beginning with 0.30 gm (1.3 mMol) 5-amino-3-(1-methylpiperidin-4-yl)pyrrolo[3,2-b]pyridine and 0.29 gm (1.56 mMol) 3-chloro-2-thiophenecarbonyl chloride, 0.28 gm (57%) of the title compound were prepared as an orange foam essentially by the procedure described in Example 4.

m.p.=255° C. (dec.)

MS(m/e): 374 (M$^+$)

Calculated for $C_{18}H_{19}ClN_4OS$: Theory: C, 57.67; H, 5.11; N, 14.94. Found: C, 57.58; H, 5.20; N, 15.32.

EXAMPLE 57

5-(N-[5-chloro-2-thiophenecarbonyl]amino)-3-(1-methylpiperidin-4-yl)pyrrolo[3,2-b]pyridine Beginning with 0.30 gm (1.3 mMol) 5-amino-3-(1-methylpiperidin-4-yl)pyrrolo[3,2-b]pyridine and 0.29 gm (1.56 mMol) 5-chloro-2-thiophenecarbonyl chloride, 0.36 gm (75%) of the title compound were prepared essentially by the procedure described in Example 4.

m.p.=117.7–120.4° C.

MS(m/e): 374 (M$^+$)

Calculated for $C_{18}H_{19}ClN_4OS$: Theory: C, 57.67; H, 5.11; N, 14.94. Found: C, 57.68; H, 5.21; N, 14.67.

EXAMPLE 58

5-(N-[3-bromo-2-thiophenecarbonyl]amino)-3-(1-methylpiperidin-4-yl)pyrrolo[3,2-b]pyridine Beginning with 0.37 gm (1.6 mMol) 5-amino-3-(1-methylpiperidin-4-yl)pyrrolo[3,2-b]pyridine and 0.45 gm (2.0 mMol) 3-bromo-2-thiophenecarbonyl chloride, 0.33 gm (49%) of the title compound were prepared essentially by the procedure described in Example 8.

m.p.=245–247° C.

MS(m/e): 420 (M+1)

Calculated for $C_{18}H_{19}BrN_4OS$: Theory: C, 51.56; H, 4.57; N, 13.36. Found: C, 51.54; H, 4.57; N, 13.31.

EXAMPLE 59

5-(N-[3-methyl-2-thiophenecarbonyl]amino)-3-(1-methylpiperidin-4-yl)pyrrolo[3,2-b]pyridine Beginning with 0.40 gm (1.74 mMol) 5-amino-3-(1-methylpiperidin-4-yl)pyrrolo[3,2-b]pyridine and 0.34 gm (2.08 mMol) 3-methyl-2-thiophenecarbonyl chloride, 0.51 gm (83%) of the title compound were prepared as a light brown foam essentially by the procedure described in Example 4. A sample was crystallized from ethanol/water for analysis.

m.p.=208.5–210.7° C.

MS(m/e): 354 (M$^+$)

Calculated for $C_{19}H_{22}N_4OS$: Theory: C, 64.38; H, 6.26; N, 15.81. Found: C, 64.14; H, 6.10; N, 15.89.

EXAMPLE 60

5-(N-[5-methyl-2-thiophenecarbonyl]amino)-3-(1-methylpiperidin-4-yl)pyrrolo[3,2-b]pyridine Beginning with 0.40 gm (1.74 mMol) 5-amino-3-(1-methylpiperidin-4-yl)pyrrolo[3,2-b]pyridine and 0.34 gm (2.08 mMol) 5-methyl-2-thiophenecarbonyl chloride, 0.53 gm (86%) of the title compound were prepared essentially by the procedure described in Example 4.

m.p.=123.2–127.4° C.

MS(m/e): 355 (M+1)

Calculated for $C_{19}H_{22}N_4OS$: Theory: C, 64.38; H, 6.26; N, 15.81. Found: C, 64.17; H, 6.17; N, 15.61.

EXAMPLE 61

5-(N-[2,5-dimethyl-4-thiazolecarbonyl]amino)-3-(1-methylpiperidin-4-yl)pyrrolo[3,2-b]pyridine Beginning with 0.34 gm (1.6 mMol) 5-amino-3-(1-methylpiperidin-4-yl)pyrrolo[3,2-b]pyridine and 0.44 gm (2.50 mMol) 2,5-dimethyl-4-thiazolecarbonyl chloride, the title compound was prepared essentially by the procedure described in Example 4.

m.p.=125–126° C.

MS(m/e): 369 (M$^+$)

Calculated for $C_{19}H_{23}N_5OS$: Theory: C, 61.76; H, 6.27; N, 18.95. Found: C, 61.80; H, 6.37; N, 18.99.

EXAMPLE 62

5-(N-[2-pyridinecarbonyl]amino)-3-(1-methylpiperidin-4-yl)pyrrolo[3,2-b]pyridine Beginning with 0.30 gm (1.30 mMol) 5-amino-3-(1-methylpiperidin-4-yl)pyrrolo[3,2-b]pyridine and 0.34 gm (1.56 mMol) 2-pyridinecarbonyl chloride, 0.098 gm (26%) of the title compound were prepared as a crystalline solid essentially by the procedure described in Example 4.

m.p.=221.0–223.3° C.

MS(m/e): 335 (M$^+$)

EXAMPLE 63

5-(N-[2-chloro-3-pyridinecarbonyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.054 mMol 2-chloro-3-pyridinecarbonyl chloride, the title compound was prepared essentially by the procedure described in Example 7.

MS(m/e): 370 (M$^+$)

EXAMPLE 64

5-(N-[6-chloro-3-pyridinecarbonyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.054 mMol 6-chloro-3-pyridinecarbonyl chloride, the title compound was prepared essentially by the procedure described in Example 7.

MS(m/e): 370 (M$^+$)

EXAMPLE 65
5-(N-[2-benzothiophenecarbonyl]amino)-3-(1-methylpiperidin-4-yl)pyrrolo[3,2-b]pyridine Beginning with 0.41 gm (1.8 mMol) 5-amino-3-(1-methylpiperidin-4-yl)pyrrolo[3,2-b]pyridine and 0.46 gm (2.33 mMol) 2-benzothiophenecarbonyl chloride, 0.32 gm (46%) of the title compound were prepared essentially by the procedure described in Example 4.
m.p.=202–204° C.
MS(m/e): 390 (M$^+$)
Calculated for $C_{22}H_{22}N_4OS$: Theory: C, 67.67; H, 6.68; N, 14.35. Found: C, 67.79; H, 5.61; N, 14.26.

EXAMPLE 66
5-(N-[3-methoxycarbonylpropionyl]amino)-3-(1-methylpiperidin-4-yl)pyrrolo[3,2-b]pyridine Beginning with 0.010 gm (0.044 mMol) 5-amino-3-(1-methylpiperidin-4-yl)pyrrolo[3,2-b]pyridine and 0.007 mL (0.057 mMol) 3-methoxycarbonylpropionyl chloride, 0.01 gm (67%) of the title compound were prepared essentially by the procedure described in Example 7.
MS(m/e): 345 (M+1)

EXAMPLE 67
5-(N-[cyclopropanecarbonyl]amino)-3-(1-piperidin-4-yl)pyrrolo[3,2-b]pyridine Beginning with 0.015 gm (0.047 mMol) 5-amino-3-(1-tert-butoxycarbonylpiperidin-4-yl)pyrrolo[3,2-b]pyridine and 0.005 mL (0.062 mMol) cyclopropanecarbonyl chloride, 5-(N-[cyclopropanecarbonyl]amino)-3-(1-tert-butoxycarbonyl-piperidin-4-yl)pyrrolo[3,2-b]pyridine was prepared essentially by the procedure described in Example 7. This compound was dissolved in 10% trifluoroacetic acid in dichloromethane and the reaction mixture was stirred at room temperature for 1 hour. The volatiles were removed under reduced pressure and the residue dissolved in methanol. This methanol solution was passed over a VARIAN BOND ELUT SCT™ (Varian, Harbor City, Calif., U.S.A.) ion exchange column which had been preactivated with 10% acetic acid in methanol. The column was washed thoroughly with methanol and then the desired product eluted with 2M ammonia in methanol. Fractions containing product were combined and concentrated under reduced pressure to provide the title compound.
MS(m/e): 284 (M$^+$)

The compounds of Examples 68–76 were prepared essentially by the procedure described in detail in Example 67.

EXAMPLE 68
5-(N-[acetyl]amino)-3-(piperidin-4-yl)pyrrolo[3,2-b]pyridine

Beginning with 0.015 gm (0.047 mMol) 5-amino-3-(1-tert-butoxycarbonylpiperidin-4-yl)pyrrolo[3,2-b]pyridine and 0.004 mL (0.062 mMol) acetyl chloride, the title compound was prepared.
MS(m/e): 258 (M$^+$)

EXAMPLE 69
5-(N-[propionyl]amino)-3-(piperidin-4-yl)pyrrolo[3,2-b]pyridine

Beginning with 0.015 gm (0.047 mMol) 5-amino-3-(1-tert-butoxycarbonylpiperidin-4-yl)pyrrolo[3,2-b]pyridine and 0.005 mL (0.062 mMol) propionyl chloride, the title compound was prepared.
MS(m/e): 273 (M$^+$)

EXAMPLE 70
5-(N-[benzoyl]amino)-3-(piperidin-4-yl)pyrrolo[3,2-b]pyridine

Beginning with 0.015 gm (0.047 mMol) 5-amino-3-(1-tert-butoxycarbonylpiperidin-4-yl)pyrrolo[3,2-b]pyridine and 0.007 mL (0.062 mMol) benzoyl chloride, the title compound was prepared.
MS(m/e): 320 (M$^+$)

EXAMPLE 71
5-(N-[4-fluorobenzoyl]amino)-3-(piperidin-4-yl)pyrrolo[3,2-b]pyridine Beginning with 0.015 gm (0.047 mMol) 5-amino-3-(1-tert-butoxycarbonylpiperidin-4-yl)pyrrolo[3,2-b]pyridine and 0.007 mL (0.062 mMol) 4-fluorobenzoyl chloride, the title compound was prepared.
MS(m/e): 338 (M$^+$)

EXAMPLE 72
5-(N-[2-thiophenecarbonyl]amino)-3-(piperidin-4-yl)pyrrolo[3,2-b]pyridine Beginning with 0.015 gm (0.047 mMol) 5-amino-3-(1-tert-butoxycarbonylpiperidin-4-yl)pyrrolo[3,2-b]pyridine and 0.006 mL (0.062 mMol) 2-thiophenecarbonyl chloride, the title compound was prepared.
MS(m/e): 326 (M$^+$)

EXAMPLE 73
5-(N-[2-furoyl]amino)-3-(piperidin-4-yl)pyrrolo[3,2-b]pyridine

Beginning with 0.015 gm (0.047 mMol) 5-amino-3-(1-tert-butoxycarbonylpiperidin-4-yl)pyrrolo[3,2-b]pyridine and 0.006 mL (0.062 mMol) 2-furoyl chloride, the title compound was prepared.
MS(m/e): 310 (M$^+$)

EXAMPLE 74
5-(N-[3-furoyl]amino)-3-(piperidin-4-yl)pyrrolo[3,2-b]pyridine

Beginning with 0.015 gm (0.047 mMol) 5-amino-3-(1-tert-butoxycarbonylpiperidin-4-yl)pyrrolo[3,2-b]pyridine and 0.008 mL (0.062 mMol) 3-furoyl chloride, the title compound was prepared.
MS(m/e): 310 (M$^+$)

EXAMPLE 75
5-(N-[3-thiophenecarbonyl]amino)-3-(piperidin-4-yl)pyrrolo[3,2-b]pyridine Beginning with 0.015 gm (0.047 mMol) 5-amino-3-(1-tert-butoxycarbonylpiperidin-4-yl)pyrrolo[3,2-b]pyridine and 0.009 mL (0.062 mMol) 3-thiophenecarbonyl chloride, the title compound was prepared.
MS(m/e): 326 (M$^+$)

EXAMPLE 76
5-(N-[4-pyridinecarbonyl]amino)-3-(piperidin-4-yl)pyrrolo[3,2-b]pyridine Beginning with 0.015 gm (0.047 mMol) 5-amino-3-(1-tert-butoxycarbonylpiperidin-4-yl)pyrrolo[3,2-b]pyridine and 0.011 gm (0.062 mMol) 4-pyridinecarbonyl chloride, the title compound was prepared.
MS(m/e): 322 (M$^+$)

EXAMPLE 77
5-(N-[cyclopropanecarbonyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.008 mL (0.080 mMol) cyclopropanecarbonyl chloride, the title compound was prepared essentially by the procedure described in Example 7.
MS(m/e): 312 (M$^+$)

EXAMPLE 78
5-(N-[acetyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.006 mL (0.080 mMol) acetyl chloride, the title compound was prepared essentially by the procedure described in Example 7.
MS(m/e): 287 (M+1)

EXAMPLE 79
5-(N-[propionyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.007 mL (0.080 mMol) acetyl chloride, the title compound was prepared essentially by the procedure described in Example 7.
MS(m/e): 301 (M+1)

EXAMPLE 80
5-(N-[benzoyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.009 mL (0.080 mMol) benzoyl chloride, the title compound was prepared essentially by the procedure described in Example 7.
MS(m/e): 349 (M$^+$)

EXAMPLE 81
5-(N-[4-fluorobenzoyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.009 mL (0.080 mMol) 4-fluorobenzoyl chloride, the title compound was prepared essentially by the procedure described in Example 7.
MS(m/e): 367 (M$^+$)

EXAMPLE 82
5-(N-[2-furoyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.008 mL (0.080 mMol) furoyl chloride, the title compound was prepared essentially by the procedure described in Example 7.
MS(m/e): 338 (M$^+$)

EXAMPLE 83
5-(N-[3-furoyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.010 mL (0.080 mMol) 3-furoyl chloride, the title compound was prepared essentially by the procedure described in Example 7.
MS(m/e): 338 (M$^+$)

EXAMPLE 84
5-(N-[2-thiophenecarbonyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.009 mL (0.080 mMol) 2-thiophenecarbonyl chloride, the title compound was prepared essentially by the procedure described in Example 7.
MS(m/e): 355 (M$^+$)

EXAMPLE 85
5-(N-[3-thiophenecarbonyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.012 mL (0.080 mMol) 3-thiophenecarbonyl chloride, the title compound was prepared essentially by the procedure described in Example 7.
MS(m/e): 355 (M$^+$)

EXAMPLE 86
5-(N-[4-pyridinecarbonyl]amino)-3-(ethylpiperidin-4-yl)pyrrolo[3,2-b]pyridine Beginning with 0.015 gm (0.061 mMol) 5-amino-3-(1-ethylpiperidin-4-yl)pyrrolo[3,2-b]pyridine and 0.014 mL (0.080 mMol) 4-pyridinecarbonyl chloride hydrochloride, the title compound was prepared essentially by the procedure described in Example 7.
MS(m/e): 350 (M$^+$)

EXAMPLE 87
5-(N-[propionyl]amino)-3-(1-propylpiperidin-4-yl)pyrrolo[3,2-b]pyridine Beginning with 0.10 gm (0.39 mMol) 5-amino-3-(1-propylpiperidin-4-yl)pyrrolo[3,2-b]pyridine and 0.040 mL (0.046 mMol) propionyl chloride, 0.099 gm (81%) of the title compound were prepared as an ivory foam essentially by the procedure described in Example 4. An analytical sample was crystallized from aqueous ethanol.
m.p.=89–91.1° C.
MS(m/e): 314 (M$^+$)
Calculated for $C_{18}H_{26}N_4O$: Theory: C, 68.76; H, 8.33; N, 17.82. Found: C, 68.73; H, 8.49; N, 17.85.

EXAMPLE 87
5-(N-[4-fluorobenzoyl]amino)-3-(1-propylpiperidin-4-yl)pyrrolo[3,2-b]pyridine Beginning with 0.10 gm (0.39 mMol) 5-amino-3-(1-propylpiperidin-4-yl)pyrrolo[3,2-b]pyridine and 0.055 mL (0.046 mMol) 4-fluorobenzoyl chloride, 0.099 gm (67%) of the title compound were prepared as an ivory foam essentially by the procedure described in Example 4. An analytical sample was crystallized from aqueous ethanol.
m.p.=216.7° C. (dec.)
MS(m/e): 380 (M$^+$)

EXAMPLE 89
5-(N-[propionyl]amino)-3-(1-isopropylpiperidin-4-yl)pyrrolo[3,2-b]pyridine Beginning with 0.10 gm (0.39 mMol) 5-amino-3-(1-isopropylpiperidin-4-yl)pyrrolo[3,2-b]pyridine and 0.040 mL (0.046 mMol) propionyl chloride, 0.092 gm (75%) of the title compound were prepared as an ivory foam essentially by the procedure described in Example 4. An analytical sample was crystallized from aqueous ethanol.
m.p.=94.1–95.8° C.
MS(m/e): 314 (M$^+$)
Calculated for $C_{18}H_{26}N_4O$: Theory: C, 68.76; H, 8.33; N, 17.82. Found: C, 68.57; H, 8.37; N, 17.67.

EXAMPLE 90
5-(N-[4-fluorobenzoyl]amino)-3-(1-isopropylpiperidin-4-yl)pyrrolo[3,2-b]pyridine Beginning with 0.10 gm (0.39 mMol) 5-amino-3-(1-isopropylpiperidin-4-yl)pyrrolo[3,2-b]pyridine and 0.055 mL (0.046 mMol) 4-fluorobenzoyl chloride, 0.085 gm (58%) of the title compound were prepared as an ivory foam essentially by the procedure described in Example 4. An analytical sample was crystallized from aqueous ethanol.

m.p.=101.0 –103.5° C.
MS(m/e): 380 (M+)
Calculated for $C_{22}H_{25}N_4OF$: Theory: C, 69.45; H, 6.62; N, 14.73. Found: C, 69.54; H, 6.66; N, 14.65.

EXAMPLE 91
5-(N-[propionyl]amino)-3-(1-butylpiperidin-4-yl)pyrrolo[3,2-b]pyridine Beginning with 0.15 gm (0.55 mMol) 5-amino-3-(1-butylpiperidin-4-yl)pyrrolo[3,2-b]pyridine and 0.058 mL (0.067 mMol) propionyl chloride, 0.062 gm (35%) of the title compound were prepared as an ivory foam essentially by the procedure described in Example 4. An analytical sample was crystallized from aqueous ethanol.
MS(m/e): 328 (M+)
Calculated for $C_{19}H_{28}N_4O$: Theory: C, 69.48; H, 8.59; N, 17.06. Found: C, 69.77; H, 8.69; N, 17.12.

EXAMPLE 92
5-(N-[4-fluorobenzoyl]amino)-3-(1-butylpiperidin-4-yl)pyrrolo[3,2-b]pyridine Beginning with 0.15 gm (0.55 mMol) 5-amino-3-(1-butylpiperidin-4-yl)pyrrolo[3,2-b]pyridine and 0.079 mL (0.067 mMol) 4-fluorobenzoyl chloride, 0.094 gm (43%) of the title compound were prepared as an ivory foam essentially by the procedure described in Example 4. An analytical sample was crystallized from aqueous ethanol.
MS(m/e): 394 (M+)
Calculated for $C_{23}H_{27}N_4OF$: Theory: C, 70.03; H, 6.90; N, 14.20. Found: C, 70.19; H, 6.75; N, 14.55.

EXAMPLE 93
5-(N-[cyclopropanecarbonyl]amino)-3-(1-(2-phenyleth-1-yl)piperidin-4-yl)pyrrolo[3,2-b]pyridine Beginning with 0.015 gm (0.047 mMol) 5-amino-3-(1-(2-phenyleth-1-yl)piperidin-4-yl)pyrrolo[3,2-b]pyridine and 0.006 mL (0.061 mMol) cyclopropanecarbonyl chloride, the title compound was prepared essentially by the procedure described in Example 7.
MS(m/e): 389 (M+1)

EXAMPLE 94
5-(N-[acetyl]amino)-3-(1-(2-phenyleth-1-yl)piperidin-4-yl)pyrrolo[3,2-b]pyridine Beginning with 0.015 gm (0.047 mMol) 5-amino-3-(1-(2-phenyleth-1-yl)piperidin-4-yl)pyrrolo[3,2-b]pyridine and 0.004 mL (0.061 mMol) acetyl chloride, the title compound was prepared essentially by the procedure described in Example 7.
MS(m/e): 363 (M+1)

EXAMPLE 95
5-(N-[propionyl]amino)-3-(1-(2-phenyleth-1-yl)piperidin-4-yl)pyrrolo[3,2-b]pyridine Beginning with 0.015 gm (0.047 mMol) 5-amino-3-(1-(2-phenyleth-1-yl)piperidin-4-yl)pyrrolo[3,2-b]pyridine and 0.005 mL (0.061 mMol) acetyl chloride, the title compound was prepared essentially by the procedure described in Example 7.
MS(m/e): 377 (M+1)

EXAMPLE 96
5-(N-[benzoyl]amino)-3-(1-(2-phenyleth-1-yl)piperidin-4-yl)pyrrolo[3,2-b]pyridine Beginning with 0.015 gm (0.047 mMol) 5-amino-3-(1-(2-phenyleth-1-yl)piperidin-4-yl)pyrrolo[3,2-b]pyridine and 0.007 mL (0.061 mMol) acetyl chloride, the title compound was prepared essentially by the procedure described in Example 7.
MS(m/e): 424 (M+)

EXAMPLE 97
5-(N-[4-fluorobenzoyl]amino)-3-(1-(2-phenyleth-1-yl)piperidin-4-yl)pyrrolo[3,2-b]pyridine Beginning with 0.015 gm (0.047 mMol) 5-amino-3-(1-(2-phenyleth-1-yl)piperidin-4-yl)pyrrolo[3,2-b]pyridine and 0.007 mL (0.061 mMol) 4-fluorobenzoyl chloride, the title compound was prepared essentially by the procedure described in Example 7.
MS(m/e): 442 (M+)

EXAMPLE 98
5-(N-[2-furoyl]amino)-3-(1-(2-phenyleth-1-yl)poperidin-4-yl)pyrrolo[3,2-b]pyridine Beginning with 0.015 gm (0.047 mMol) 5-amino-3-(1-(2-phenyleth-1-yl)piperidin-4yl)pyrrolo[3,2-b]pyridine and 0.006 mL (0.061 mMol) furoyl chloride, the title compound was prepared essentially by the procedure described in Example 7. MS(m/e): 414(M+)

EXAMPLE 99
5-(N-[3-furoyl]amino)-3-(1-(2-phenyleth-1-yl)piperidin-4-yl)pyrrolo[3,2-b]pyridine Beginning with 0.015 gm (0.047 mMol) 5-amino-3-(1-(2-phenyleth-1-yl)piperidin-4-yl)pyrrolo[3,2-b]pyridine and 0.008 mL (0.061 mMol) 3-furoyl chloride, the title compound was prepared essentially by the procedure described in Example 7. MS(m/e): 414(M+)

EXAMPLE 100
5-(N-[2-thiophenecarbonyl]amino)-3-(1-(2-phenyleth-1-yl)piperidin-4-yl)pyrrolo[3,2-b]pyridine Beginning with 0.015 gm (0.047 mMol) 5-amino-3-(1-(2-phenyleth-1-yl)piperidin-4-yl)pyrrolo[3,2-b]pyridine and 0.006 mL (0.061 mMol) 2-thiophenecarbonyl chloride, the title compound was prepared essentially by the procedure described in Example 7. MS(m/e): 431(M+1)

EXAMPLE 101
5-(N-[3-thiophenecarbonyl]amino)-3-(1-(2-phenyleth-1-yl)piperidin-4-yl(pyrrolo[3,2-b]pyridine Beginning with 0.015 gm (0.047 mMol) 5-amino-3-(1-(2-phenyleth-1-yl)piperidin-4-yl)pyrrolo[3,2-b]pyridine and 0.009 mL (0.061 mMol) 3-thiophenecarbonyl chloride, the title compound was prepared essentially by the procedure described in Example 7. MS(m/e): 431(M+1)

EXAMPLE 102
5-(N-[4-pyridinecarbonyl]amino)-3-(1-(2-phenyleth-1-yl)piperidin-4-yl)pyrrolo[3,2-b]pyridine Beginning with 0.015 gm (0.047 mMol) 5-amino-3-(1-(2-phenyleth-1-yl)piperidin-4-yl)pyrrolo[3,2-b]pyridine and 0.011 mL (0.061 mMol) 4-pyridinecarbonyl chloride hydrochloride, the title compound was prepared essentially by the procedure described in Example 7. MS(m/e): 426 (M+1)

EXAMPLE 103
5-(N-[4-fluorobenzoyl]amino)-3-(1-methyl-1,2,3,6-tetrahydropyridin-4-yl)pyrrolo[3,2-b]pyridine Beginning with 0.200 gm (0.88 mMol) 5-amino-3-(1-methyl-1,2,3,6-tetrahydropyridin-4-yl)pyrrolo[3,2-b]pyridine and 0.114 mL (0.96 mMol) 4-fluorobenzoyl chloride, 0.260 gm (84%) of the title compound were prepared as an ivory solid essentially by the procedure described in Example 4. An analytical sample was crystallized from aqueous ethanol. m.p.=215° C. (dec.) MS(m/e): 350(M$^+$) Calculated for $C_{20}H_{19}N_4OF$: Theory: C, 68.56; H, 5.47; N, 15.99. Found: C, 68.57; H, 5.66; N, 16.01.

EXAMPLE 104

5-(N-[4-pyridinecarbonyl]amino)-3-(1-methyl-1,2,3,6-tetrahydropyridin-4-yl)pyrrolo[3,2-b]pyridine Beginning with 0.200 gm (0.88 mMol) 5-amino-3-(1-methyl-1,2,3,6-tetrahydropyridin-4-yl)pyrrolo[3,2-b]pyridine and 0.188 gm (1.06 mMol) 4-pyridinecarbonyl chloride hydrochloride, 0.180 gm (61%) of the title compound were prepared as an ivory solid essentially by the procedure described in Example 8. An analytical sample was crystallized from aqueous ethanol. m.p.=202.8° C. (dec.) MS(m/e): 333(M$^+$) Calculated for $C_{19}H_{19}N_5O$: Theory: C, 68.45; H, 5.74; N, 21.01. Found: C, 68.28; H, 5.68; N, 21.21.

EXAMPLE 105

5-(N-[cyclopropanecarbonyl]amino)-3-(1-ethyl-1,2,3,6-tetrahydropyridin-4yl)pyrrolo[3,2-b]pyridine Beginning with 0.015 gm (0.062 mMol) 5-amino-3-(1-ethyl-1,2,3,6-tetrahydropyridin-4-yl)pyrrolo[3,2-b]pyridine and 0.006 mL (0.068 mMol) cyclopropanecarbonyl chloride, the title compound was prepared essentially by the procedure described in Example 7. MS(m/e): 311(M+1)

EXAMPLE 106

5-N-[acetyl]amino-3-(1-ethyl-1,2,3,6-tetrahydropyridin-4-yl)pyrrolo[3,2-b]pyridine Beginning with 0.015 gm (0.062 mMol) 5-amino-3-(1-ethyl-1,2,3,6-tetrahydropyridin-4-yl)pyrrolo[3,2-b]pyridine and 0.005 mL (0.068 mMol) acetyl chloride, the title compound was prepared essentially by the procedure described in Example 7. MS(m/e): 285(M+1)

EXAMPLE 107

5-(N-[benzoyl]amino)-3-(1-ethyl-1,2,3,6-tetrahydropyridin-4-yl)pyrrolo[3,2-b]pyridine Beginning with 0.015 gm (0.062 mMol) 5-amino-3-(1-ethyl-1,2,3,6-tetrahydropyridin-4-yl)pyrrolo[3,2-b]pyridine and 0.008 mL (0.068 mMol) benzoyl chloride, the title compound was prepared essentially by the procedure described in Example 7. MS(m/e): 346(M+1)

EXAMPLE 108

5-(N-[4-fluorobenzoyl]amino)-3-(1-ethyl-1,2,3,6-tetrahydropyridin-4-yl)pyrrolo[3,2-b]pyridine Beginning with 0.015 gm (0.062 mMol) 5-amino-3-(1-ethyl-1,2,3,6-tetrahydropyridin-4-yl)pyrrolo[3,2-b]pyridine and 0.008 mL (0.068 mMol) 4-fluorobenzoyl chloride, the title compound was prepared essentially by the procedure described in Example 7. MS(m/e): 365(M+1)

EXAMPLE 109

5-(N-[2-furoyl]amino)-3-(1-ethyl-1,2,3,6-tetrahydropyridin-4-yl)pyrrolo[3,2-b]pyridine Beginning with 0.015 gm (0.062 mMol) 5-amino-3-(1-ethyl-1,2,3,6-tetrahydropyridin-4-yl)pyrrolo[3,2-b]pyridine and 0.007 mL (0.068 mMol) 2-furoyl chloride, the title compound was prepared essentially by the procedure described in Example 7. MS(m/e): 337(M+1)

EXAMPLE 110

5-(N-[2-thiophenecarbonyl]amino)-3-(1-ethyl1,2,3,6-tetrahydropyridin-4-yl)pyrrolo[3,2-b]pyridine Beginning with 0.015 gm (0.062 mMol) 5-amino-3-(1-ethyl-1,2,3,6-tetrahydropyridin-4-yl)pyrrolo[3,2-b]pyridine and 0.007 mL (0.068 mMol) 2-thiophenecarbonyl chloride, the title compound was prepared essentially by the procedure described in Example 7. MS(m/e): 353(M+1)

EXAMPLE 111

5-(N-[ethoxycarbonyl]amino)-3-(1-ethyl-1,2,3,6-tetrahydropyridin-4-yl)pyrrolo[3,2-b]pyridine Beginning with 0.015 gm (0.062 mMol) 5-amino-3-(1-ethyl-1,2,3,6-tetrahydropyridin-4yl)pyrrolo[3,2-b]pyridine and 0.006 mL (0.068 mMol) ethyl chloroformate, the title compound was prepared essentially by the procedure described in Example 7. MS(m/e): 315(M+1)

EXAMPLE 112

5-(N-[cyclopropylcarbonyl]amino)-3-(1-(2-phenyleth-1-yl)-1,2,3,6-tetrahydropyridin-4-yl)pyrrolo[3,2-b]pyridine Beginning with 0.015 gm (0.047 mMol) 5-amino-3-(1-(2-phenyleth-1-yl)-1,2,3,6-tetrahydropyridin-4-yl)pyrrolo[3,2-b]pyridine and 0.006 mL (0.061 mMol) cyclopropylcarbonyl chloride, the title compound was prepared essentially by the procedure described in Example 7. MS(m/e): 387(M+1)

EXAMPLE 113

5-(N-[acetyl]amino)-3-(1-(2-phenyleth-1-yl)-1,2,3,6-tetrahydropyridin-4-yl)pyrrolo[3,2-b]pyridine Beginning with 0.015 gm (0.047 mMol) 5-amino-3-(1-(2-phenyleth-1-yl)-1,2,3,6-tetrahydropyridin-4-yl)pyrrolo[3,2-b]pyridine and 0.004 mL (0.061 mMol) acetyl chloride, the title compound was prepared essentially by the procedure described in Example 7. MS(m/e): 361(M+1)

EXAMPLE 114

5-(N-[propionyl]amino)-3-(1-(2-phenyleth-1-yl)-1,2,3,6-tetrahydropyridin-4-yl)pyrrolo[3,2-b]pyridine Beginning with pb 0.015gm (0.047 mMol) 5-amino-3-(1-(2-phenyleth-1-yl)-1,2,3,6-tetrahydropyridin-4-yl)pyrrolo[3,2-b]pyridine and 0.005 mL (0.061 mMol) propionyl chloride, the title compound was prepared essentially by the procedure described in Example 7. MS(M/e): 375(M+1)

EXAMPLE 115

5-(N-[benzoyl]amino)-3-(1-(2-phenyleth-1-yl)-1,2,3,6-tetrahydropyridin-4-yl)pyrrolo[3,2-b]pyridine Beginning with 0.015 gm (0.047 mMol) 5-amino-3-(1-(2-phenyleth-1-yl)-1,2,3,6-tetrahydropyridin-4-yl)pyrrolo[3,2-b]pyridine and 0.007 mL (0.061 mMol) benzoyl chloride, the title compound was prepared essentially by the procedure described in Example 7. MS(M/e): 423(M+1)

EXAMPLE 116

5-(N-[4-fluorobenzoyl]amino)-3-(1-(2-phenyleth-1yl)-1,2,3,6-tetrahydropyridin-4yl)pyrrolo[3,2-b]pyridine Beginning with 0.015 gm (0.047 mMol) 5-amino-3-(1-(2-phenyleth-1-yl)-1,2,3,6-tetrahydropyridin-4-yl)pyrrolo[3,2-b]pyridine and 0.007 mL (0.061 mMol) 4-fluorobenzoyl chloride, the title compound was prepared essentially by the procedure described in Example 7. MS(m/e): 441(M+1)

EXAMPLE 117

5-(N-[2-furoyl]amino)-3-(1-(2-phenyleth-1-yl)-1,2,3,6-tetrahydropyridin-4-yl)pyrrolo[3,2-b]pyridine Beginning with 0.015 gm (0.047 mMol) 5-amino-3-(1-(2-phenyleth-1-yl)-1,2,3,6-tetrahydropyridin-4-yl)pyrrolo[3,2-b]pyridine and 0.006 mL (0.061 mNol) 2-furoyl chloride, the title compound was prepared essentially by the procedure described in Example 7. MS(m/e): 413(M+1)

EXAMPLE 118

5-(N-[3-furoyl]amino)-3-(1-(2-phenyleth-1yl)-1,2,3,6-tetrahydropyridin-4-yl)pyrrolo[3,2-b]pyridine Beginning with 0.015 gm (0.047 mMol) 5-amino-3-(1-(2-phenyleth-1-yl)-1,2,3,6-tetrahydropyridin-4-yl)pyrrolo[3,2-b]pyridine and 0.009 mL (0.061 mMol) 3-furoyl chloride, the title compound was prepared essentially by the procedure described in Example 7. MS(m/e): 413(M+1)

EXAMPLE 119

5-(N-[2-thiophenecarbonyl]amino)-3-(1-(2-phenyleth-1-yl)-1,2,3,6-tetrahydropyridin-4-yl)pyrrolo[3,2-b]pyridine Beginning with 0.015 gm (0.047 mMol) 5-amino-3-(1-(2-phenyleth-1-yl)-1,2,3,6-tetrahydropyridin-4-yl)pyrrolo[3,2-b]pyridine and 0.007 mL (0.061 mMol) 2-thiophenecarbonyl chloride, the title compound was prepared essentially by the procedure described in example 7. MS(m/e): 429($M^+$)

EXAMPLE 120

5-(N-[3 -thiophenecarbonyl]amino)-3-(1-(2-phenyleth-1yl)-1,2,3,6-tetrahydropyridin-4-yl)pyrrolo[3,2-b]pyridine Beginning with 0.015 gm (0.047 mMol) 5-amino-3-(1-(2-phenyleth-1-yl)-1,2,3,6-tetrahydropyridin-4-yl)pyrrolo[3,2-b]pyridine and 0.009 mL (0.061 mMol) 3-thiophenecarbonyl chloride, the title compound was prepared essentially by the procedure described in Example 7. MS(m/e): 429($M^+$)

EXAMPLE 121

5-(N-[4-pyridinecarbonyl]amino)-3-(1-(2-phenyleth-2-yl)-1,2,3,6-tetrahydropyridin-4-yl)pyrrolo[3,2-b]pyridine Beginning with 0.015 gm (0.047 mMol) 5-amino-3-(1-(2-phenyleth-1-yl)-1,2,3,6-tetrahydropyridin-4-yl)pyrrolo[3,2-b]pyridine and 0.011 mL (0.061 mMol) 4-pyridinecarbonyl chloride, the title compound was prepared essentially by the procedure described in Example 7. MS(m/e): 424(M+1)

EXAMPLE 122

N-[methyl]-N'-[3-(1-methylpiperidin-4yl)pyrrolo[3,2-b]pyridin-5-yl]urea

A solution of 0.15 gm (0.65 mMol) 5-amino-3-(1-methyl-piperidin-4yl)pyrrolo[3,2-b]pyridine and 0.046 mL (0.78 mMol) methyl isocyanate in 6 mL 5:1 tetrahydrofuran:dimethylformamide was stirred at room temperature for 5 hours. At this point an additional 0.020 mL methyl isocyanate were added and stirring continued for another 3.5 hours. The reaction mixture was then concentrated under reduced pressure. The residue was partitioned between 3:1 chloroform:isopropanol and 1N sodium hydroxide. The phases were separated and the aqueous phase extracted well with 3:1 chloroform:isopropanol. The organic phases were combined, washed with saturated aqueous sodium chloride, dried over magnesium sulfate and concentrated under reduced pressure. The residue was subjected to radial chromatography (2mm silica gel plate), eluting with dichloromethane containing from 20–40% methanol and 1% ammonium hydroxide. Fractions shown to contain produce were combined and concentrated under reduced pressure. The residue was crystallized from aqueous ethanol to provide 0.043 gm (34%) of the title compound. m.p.= 228.8–230.4° C. MS(m/e): 288(M+1) Calculated for $C_{15}H_{21}N_5O$: Theory: C, 62.70; H, 7.37; N, 24.37. Found: C, 62.49; H, 7.29; N, 24.40.

EXAMPLE 123

N-[ethyl]-N'-[3-(1-methylpiperidin-4yl)pyrrolo[3,2-b]pyridin-5-yl]urea

Beginning with 0.15 gm (0.65 mMol) 5-amino-3-(1-methyl-piperidin-4-yl)pyrrolo[3,2-b]pyridine and 0.067 mL (0.85 mMol) ethyl isocyanate, 0.137 gm (70%) of the title compound were recovered essentially by the procedure of Example 122. An analytical sample was crystallized from aqueous ethanol. m.p.=212.6° C. (dec.) MS(m/e): 301($M^+$) Calculated for $C_{16}H_{23}N_5O$: Theory: C, 63.76; H, 7.69; N, 23.24. Found: C, 63.29; H, 7.98; N, 22.89

EXAMPLE 124

N-[propyl]-N'-[3-(1-methylpiperidin-4-yl)pyrrolo[3,2-b]pyridin-5yl]urea

Beginning with 0.15 gm (0.65 mMol) 5-amino-3-(1-methyl-piperidin-4-yl)pyrrolo[3,2-b]pyridine and 0.073 mL (0.78 mMol) propyl isocyanate, 0.107 gm (52%) of the title compound were recovered essentially by the procedure of Example 122. An analytical sample was crystallized from aqueous ethanol. m.p.=181° C. (dec.) MS(m/e): 315($M^+$) Calculated for $C_{17}H_{25}N_5O$: Theory: C, 64.74; H, 7.99; N, 22.2. Found: C, 64.51; H, 7.77; N, 22.46.

EXAMPLE 125

N-[butyl]-N'-[3-(1-methylpiperidin-4-yl) pyrrolo[3,2-b]pyridin-5-yl]urea

Beginning with 0.15 gm (0.65 mMol) 5-amino-3-(1-methyl-piperidin-4-yl)pyrrolo[3,2-b]pyridine and 0.088 mL (0.78 mMol) butyl isocyanate, 0.168 gm (78%) of the title compound were recovered essentially by the procedure of Example 122. An analytical sample was crystallized from aqueous ethanol. MS(m/e): 329($M^+$)

EXAMPLE 126

N-[isopropyl]-N'-[3-(1-methylpiperidin-4-yl)pyrrolo[3,2-b]pyridin-5yl]urea

Beginning with 0.15 gm (0.65 mMol) 5-amino-3-(1-methyl-piperidin-4-yl)pyrrolo[3,2-b]pyridine and 0.077 mL (0.78 mMol) isopropyl isocyanate, 0.146 gm (71%) of the title compound were recovered essentially by the procedure of Example 122. An analytical sample was crystallized from aqueous ethanol. m.p.=217–219° C. (dec.) MS(m/e): 315 ($M^+$) Calculated for $C_{17}H_{25}N_5O$: Theory: C, 64.74; H, 7.99; N, 22.20; Found: C, 64.84; H, 8.06; N, 22.44.

EXAMPLE 127

N-[prop-1-en-3-yl]-N'-[3-(1-methylpiperidin-4-yl)pyrrolo[3,2-b]pyridin-5-yl]urea Beginning with 0.15 gm (0.65 mMol) 5-amino-3-(1-methyl-piperidin-4-yl)pyrrolo[3,2-b]pyridine and 0.070 mL (0.78 mMol) prop-1-en-3yl isocyanate, 0.149 gm (73%) of the title compound were recovered essentially by the procedure of Example 122. An analytical sample was crystallized from aqueous ethanol. m.p.=203° C. (dec.) MS(m/e): 313($M^+$) Calculated for $C_{17}H_{23}N_5O$: Theory: C, 65.15; H, 7.40; N, 22.35. Found: C, 65.15; H, 7.65; N, 22.22.

EXAMPLE 128

N-[phenyl]-N'-[3-(1-methylpiperidin-4-yl)pyrrolo[3,2-b]pyridin-5]urea

Beginning with 0.15 gm (0.65 mMol) 5-amino-3-(1-methyl-piperidin-4-yl)pyrrolo[3,2-b]pyridine and 0.092 mL (0.85 mMol) phenyl isocyanate, 0.137 gm (60%) of the title compound were recovered essentially by the procedure of Example 122. An analytical sample was crystallized from methanol. m.p.=247° C. (dec.) MS(m/e): 349($M^+$) Calculated for $C_{20}H_{23}N_5O$: Theory: C, 68.74; H, 6.63; N, 20.04. Found: C, 68.96; H, 6.68; N, 20.07.

EXAMPLE 129

N-[4-fluorophenyl]-N'-[3-(1-methylpiperidin-4-yl)pyrrolo[3,2-b]pyridin-5yl]urea

Beginning with 0.15 gm (0.65 mMol) 5-amino-3-(1-methyl-piperidin-4-yl)pyrrolo[3,2-b]pyridine and 0.096 mL (0.85 mMol) 4-fluorophenyl isocyanate, 0.176 gm (74%) of the title compound were recovered essentially by the procedure of Example 122. An analytical sample was crystallized from methanol. m.p.=245.8° C. (dec.) MS(m/e): 367 ($M^+$) Calculated for $C_{20}H_{22}N_5OF$: Theory: C, 65.38; H, 6.03; N, 19.06. Found: C, 65.36; H, 6.23; N, 18.91.

EXAMPLE 130

N-[ethyl]-N'-[3-(1-methylpiperidin-4-yl)pyrrolo[3,2-b]pyridin-5yl]thiourea

Beginning with 0.15 gm (0.65 mMol) 5-amino-3-(1-methyl-piperidin-4-yl)pyrrolo[3,2-b]pyridine and 0.068 mL (0.78 mMol) ethyl isothiocyanate, 0.032 gm (10%) of the title compound were recovered essentially by the procedure of Example 122. An analytical sample was crystallized from aqueous ethanol. MS(m/e): 317($M^+$)

EXAMPLE 131

5-(N-[ethoxycarbonyl]amino)-3-(1-methylpiperidin-4-yl)pyrrolo[3,2-b]pyridine

Beginning with 0.010 gm (0.044 mMol) 5-amino-3-(1-methylpiperidin-4-yl)pyrrolo[3,2-b]pyridine and 0.005 mL (0.053 mMol) ethyl chloroformate, the title compound was prepared essentially by the procedure described in Example 7. MS(m/e): 303(M+1)

EXAMPLE 132

5-(N-[isobutoxycarbonyl]amino)-3-(1-methylpiperidin-4-yl)pyrrolo[3,2-b]pyridine

Beginning with 0.010 gm (0.044 mMol) 5-amino-3-(1-methylpiperidin-4-yl)pyrrolo[3,2-b]pyridine and 0.007 mL (0.053 mMol) isobutyl chloroformate, the title compound was prepared essentially by the procedure described in Example 7. MS(m/e): 331(M+1)

EXAMPLE 133

5-(N-[prop-1-en-3-yloxycarbonyl]amino)-3-(piperidin-4-yl)pyrrolo[3,2-b]pyridine

A mixture of 4.0 gm (12.6 mMol) 5-amino-3-(1-tert-butoxycarbonylpiperidin-4-yl)pyrrolo[3,2-b]pyridine and 2.7 mL (25.2 mMol) allyl chloroformate in 200 mL pyridine was heated at 50° C. for 5 hours. At this point an additional 2 mL of allyl chloroformate were added and heating was continued for another 1.5 hours. The reaction mixture was concentrated under reduced pressure and the resulting residue partitioned between 1N sodium hydroxide and chloroform. The phases were separated and the aqueous phase was extracted well with chloroform. The organic phases were combined, washed with saturated aqueous sodium chloride, dried over sodium sulfate and concentrated under reduced pressure. This residue was dissolved in 2M ammonia in methanol for two hours. The reaction mixture was concentrated under reduced pressure and the residue subjected to flash silica gel chromatography, eluting with dichloromethane containing from 2–5% methanol and 1% ammonium hydroxide. Fractions containing produce were combined and concentrated under reduced pressure. The residue was crystallized from aqueous ethanol to provide 2.9 gm (60%) 5-(N-[prop-1-en-3-yloxycarbonyl]amino)-3-(1-tert-butoxycarbonylpiperidin-4-yl)pyrrolo[3,2-b]pyridine. MS(m/e): 400($M^+$) Calculated for $C_{21}H_{28}N_4O_4$: Theory: C, 62.98; H, 7.05; N, 13.99. Found: C, 63.06; H, 7.20; N, 14.11.

Deprotection

A solution of 0.75 cm (1.87 mMol) 5-(N-[prop-1-en-3-yloxycarbonyl]amino)-3-(1-tert-butoxycarbonylpiperidin-4-yl)pyrrolo[3,2-b]pyridine in 5 mL dichloromethane was cooled to 0° C. To this solution were then added 5 mL trifluoroacetic acid and the reaction mixture was allowed to warm gradually to room temperature. After 2 h ours the reaction mixture was concentrated under reduced pressure to provide 0.53 gm (95%) of the title compound as a white solid.

EXAMPLE 134

5-(N-[phenylsulfonyl]amino)-3-(1-methylpiperidin-4-yl)pyrrolo[3,2-b]pyridine

Beginning with 0.40 gm (1.74 mMol) 5-amino-3-(1-methylpiperidin-4yl)pyrrolo[3,2-b]pyridine and 0.267 mL (2.09 mMol) phenylsulfonyl chloride, 0.493 gm (76%) of the title compound were prepared as an orange solid essentially by the procedure described in Example 4. An analytical sample was crystallized from aqueous ethanol. m.p.= 148.1–149.7° C. MS(m/e): 371(M+1) Calculated for $C_{19}H_{22}N_4O_2S$: theory: C, 61.60; H, 5.99; N, 15.12. Found: C, 61.87; H, 6.26; N, 15.29.

The ability of the compounds of this invention to bind to the 5-$HT_{1F}$ receptor subtype was measured essentially as described in U.S. Pat. No. 5,521,196.

Membrane Preparation: Membranes were prepared from transfected Ltk-cells which were grown to 100% confluency. The cells were washed twice with phosphate-buffered saline, scraped from the culture dishes into 5 mL of ice-cold phosphate-buffered saline, and centrifuged at 200×g for 5 minutes at 40° C. The pellet was resuspended in 2.5 mL of ice-cold Tris buffer (20 mM Tris HCl, pH=7.4 at 23° C. mM EDTA) and homogenized with a Wheaton tissue grinder. The lysate was subsequently centrifuged at 200×g for 5 minutes at 4° C. to pellet large fragments which were discarded. The supernatant was collected anc entrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding: [$^3$H-5-HT] binding was performed using slight modifications of the 5-HT$_{1D}$ assay conditions reported by Herrick-Davis and Titeler (*J. Neurochem.*, 50, 1624–1631 (1988) with the omission of masking ligands. Radioligand binding studies were achieved at 37° C. in a total volume of 250 μL of buffer (50 mM Tris, 10 mM MgCl$_2$, 0.2 mM EDTA, 10 μM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10–20 μg). The reaction was terminated by rapid filtration through presoaked (0.5% polyethyleneimine) filters using 48R Cell Brandel Harvester (Gaithersburg, Md.). Subsequently, filters were washed for 5 seconds with ice cold buffer (50 nM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation (*Biochem. Pharmacol.*, 22, 3099–3108 (1973). All experiments were performed in triplicate.

Representative compounds of this invention were found to have affinity for the 5-HT$_{1F}$ receptor as measured by the procedure described supra.

As was reported by R. L. Weinshank, et al., WO93.14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Agonist activation of G-protein-coupled receptors also results in the release of DGP from the α-subunit of the G protein and the subsequent binding of GTP. The binding of the stable analog [$^{35}$S]GTPγS is an indicator of this receptor activation.

Membrane Preparation

Mouse LM(tk-)cells stably transfected with the human 5-HT$_{1F}$ receptor and grown in suspension were harvested by centrifugation, resuspended in 50 mM Tris-HCl, pH 7.4, in aliquots of 2×10$^8$ cells and frozen at −70° C. until the day of the assay. On the assay day, an aliquot of cells was thawed, resuspended in 35 mL of 50 mM Tris-HCl, pH 7.4, and centrifuged at 39,800×g for 10 minutes at 4° C. The resulting pellet was resuspended in 50 mM Tris-HCl, pH 7.4, incubated for 10 minutes at 37° C. and centrifuged at 39,800×g for 10 minutes at 4° C. The pellet was resuspended and centrifuged once more, with the final pellet being resuspended in 4 mM MgCl$_2$, 160 mM NaCl, 0.267 mM EGTA, 67 mM Tris-HCl, pH 7.4, such that a 200 μL aliquot contained contained approximately 15–25 μg protein.

[$^{35}$S]GTPγS Binding

All incubations were performed intriplicate in a total volume of 800 μL. Drug dilution in water, 200 μL, spanning 6 log units, was added to 400 μL of Tris-HCl, pH 7.4, containing 3 mM MgCl$_2$, 120 mM NaCl, 0.2 mM EGTA, 10 μM GDP, and 0.1 nM [$^{35}$S]GTPγS. Membrane homogenate, 200 μL, was added and then the tubes were incubated for 30 minutes at 37° C. Using a Brandel cell harvester (model MB-48R, Brandel, Gaithersburg, Md.), the incubations were then terminated by vacuum filtration through Whatman GF/B filters which had been wet with water or 20 nM Na$_4$P$_2$O$_7$ and precooled with 4 mL of ice-cold 50 mM Tris-HCl, pH 7.4. The filters were then washed rapidly with 4 mL of ice-cold 50 mM Tris-Hcl, pH 7.4. the amount of radioactivity captured on the filters were determined by liquid scintillation spectrometry using an LS6000IC (Beckman Instruments, Fullerton, Calif.). GTPγS, 10 μM, defined nonspecific binding. Protein was determined by the method of Bradford (*Anal. BIochem.*, 72, 248–254 (1976).

Statistical Analysis

Efficacy values for test compounds were expressed as the percent binding relative to 10 μM 5-HT. Nonlinear regression analysis was performed on the concentration response curves using a four parameter logistic equation described by De Lean et al., (*Mol Pharamacol.*, 21, 5–16 (1982). Analysis of variance, followed by the Tukey-Kramer Honestly Significant Difference test (JMP; SAS Institute Inc., Cary, N.C.) was performed on the pEC$_{50}$ values and the E$_{max}$ values.

Representative compounds of the present invention were tested in the [$^{35}$S]GTPγS assay and were found to be agonists of the 5-HT$_{1F}$ receptor.

The discovery that the pain associated with migraine and associated disorders is inhibited by activation of the 5-HT$_{1F}$ receptor by administration of the 5-HT$_{1F}$ agonists required the analysis of data from diverse assays of pharmacological activity. To establish that the 5-HT$_{1F}$ receptor subtype is responsible for mediating neurogenic meningeal extravasation which leads to the pain of migraine, the binding affinity of a panel of compounds to serotonin receptors was measured first, using standard procedures. For example, the ability of a compound to bind to the 5-HT$_{1F}$ receptor subtype was performed as described supra. For comparison purposes, the binding affinities of compounds to the 5-HT$_{1D\alpha}$, 5-HT$_{1D\beta}$, and 5-HT$_{1E}$ receptors were also determined as described supra, except that different cloned receptors were employed in place of the 5-HT$_{1F}$ receptor clone employed therein. The same panel was then tested in the cAMP assay to determine their agonist or antagonist character. Finally, the ability of these compounds to inhibit neuronal protein extravasation, a functional assay for migraine pain, was measured.

The panel of compounds used in this study represents distinct structural classes of compounds which were shown to exhibit a wide range of affinities for the serotonin receptors assayed. Additionally, the panel compounds were shown to have a wide efficacy range in the neuronal protein extravasation assay as well. The panel of compounds selected for this study are described below.

49

Compound I

3-[2-(dimethylamino)ethyl]-N-methyl-1H-indole-5-methanesulfonamide butane-1,4-dioate (1:1) (Sumatriptan succinate)

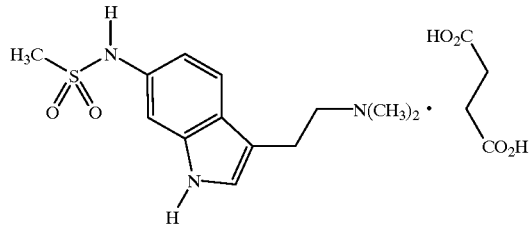

Sumatriptan succinate is commercially available as Imitrex™ or may be prepared as described in U.S. Pat. No. 5,037,845, issued Aug. 6, 1991, which is herein incorporated by reference in its entirety.

Compound II 5-fluoro-3-(1-(2-(1-methyl-1H-pyrazol-4-yl)ethyl)-4-piperidinyl)-1H-indole hydrochloride

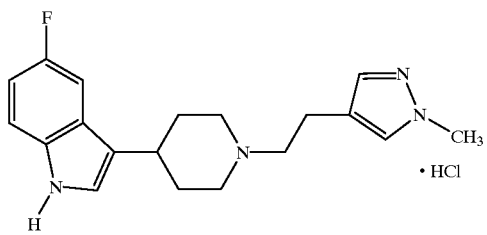

Compound III 5-hydroxy-3-(4-piperidinyl)-1H-indole oxalate

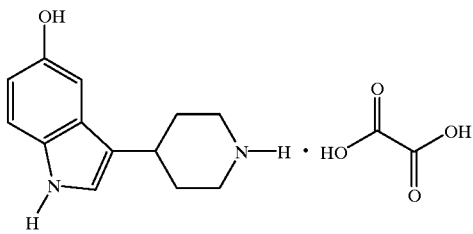

Compound IV 8-chloro-2-diethylamino-1,2,3,4-tetrahydronaphthalene hydrochloride

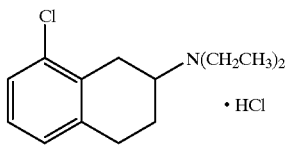

50

Compound V 6-hydroxy-3-dimethylamino-1,2,3,4-tetrahydrocarbazole

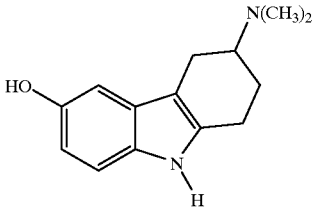

The preparation of Compounds II–V are described in U.S. Pat. No. 5,521,196, issued May 28, 1996, which is herein incorporated by reference in its entirety.

Binding Assays

The binding affinities of compounds for various serotonin receptors were determined essentially as described above except that different cloned receptors are employed in place of the $5\text{-HT}_{1F}$ receptor clone employed therein. The results of these binding experiments are summarized in Table I.

TABLE I

BINDING TO SEROTONIN (5HT$_1$) RECEPTOR SUBTYPES ($k_i$ nM)

cAMP Formation

As was reported by R. L. Weinshank, et al., WO93/14201, the $5\text{-HT}_{1F}$ receptor is functionally coupled to a G-protein as measured by the ability of serotonin and serotonergic drugs to inhibit forskolin stimulated cAMP production in NIH3T3 cells transfected with the $5\text{-HT}_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. (N. Adham, et al., supra,; R. L. Weinshank, et al., *Proceedings of the*

| Compound | 5-HT$_{1D\alpha}$ | 5-HT$_{1D\beta}$ | 5-HT$_{1E}$ | 5-HT$_{1F}$ |
|---|---|---|---|---|
| I | 4.8 | 9.6 | 2520.0 | 25.7 |
| II | 21.7 | 53.6 | 50.3 | 2.5 |
| III | 163.2 | 196.5 | 3.9 | 22.0 |
| IV | 13.5 | 145.3 | 813.0 | 129.2 |
| V | 791.0 | 1683.0 | 73.6 | 10.3 |

*National Academy of Sciences (U.S.A.)*, 89, 3630–3634 (1992)), and the references cited therein.

Measurement of cAMP Formation

Transfected NIH3T3 cells (estimated Bmax from one point competition studies=488 fmol/mg of protein) were incubated in DMEM, 5mM theophylline, 10 mM HEPES (4-[2-hydroxyethyl]-1-piperazineethanesulfonic acid) and 10 μM pargyline for 20 minutes at 37° C., 5% $CO_2$. Drug does-effect curves were then conducted by adding 6 different final concentrations of drug, followed immediately by the addition of forskolin (10 μM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 µM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software.

All of the compounds of the panel were tested in the cAMP formation assay described supra and all were found to be agonists of the 5-HT$_{1F}$ receptor.

Protein Extravasation

Harlan Sprague-Dawley rats (225–325 g) or guinea pigs from Charles River Laboratories (225–325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EGG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were cover-slipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 µm steps) on each dural sample. The mean and standard deviation of the measurements was determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side dura was calculated. Saline controls yielded a ratio of approximately 2.0 in rats and 1.8 in guinea pigs. In contrast, a compound which effectively prevented the extravsation in the dura from the stimulated side would have a ratio of approximately 1.0. A dose-response curve was generated and the dose that inhibited the extravasation by 50% (ID$_{50}$) was approximated. This data is presented in TABLE II.

TABLE II

Inhibition of Protein Extravasation (ID$_{50}$ mMol/kg)

| Compound | i.v. ID$_{50}$ (mMol/kg) |
| --- | --- |
| I | $2.6 \times 10^{-8}$ |
| II | $8.6 \times 10^{-10}$ |
| III | $8.9 \times 10^{-9}$ |
| IV | $1.2 \times 10^{-7}$ |
| V | $8.7 \times 10^{-9}$ |

To determine the relationship of binding at various serotonin receptors to inhibition of neuronal protein extravasation, the binding affinity of all of the compounds to each of the 5-HT$_{1D\alpha}$, 5-HT$_{1D\beta}$, 5-HT$_{1E}$ and 5-HT$_{1F}$ receptors was plotted against their ID$_{50}$ in the protein extravasation model. A linear regression analysis was performed on each set of data and a correlation factor, $R^2$, calculated. The results of this analysis are summarized in Table III.

TABLE III

Correlation Factor ($R^2$) for Specific 5-HT$_1$ Subtype Binding Affinity vs Inhibition of Protein Extravasation

| 5-HT$_1$ Subtype | Correlation Factor ($R^2$) |
| --- | --- |
| 5-HT$_{1D\alpha}$ | 0.07 |
| 5-HT$_{1D\beta}$ | 0.001 |
| 5-HT$_{1E}$ | 0.31 |
| 5-HT$_{1F}$ | 0.94 |

An ideally linear relationship would generate a correlation factor of 1.0, indicating a cause and effect relationship between the two variables. The experimentally determined correlation factor between inhibition of neuronal protein extravasation and 5-HT$_{1F}$ binding affinity is 0.94. This nearly ideal dependence of the ID$_{50}$ in the protein extravasation model on binding affinity to the 5-HT$_{1F}$ receptor clearly demonstrates that the 5-HT$_{1F}$ receptor mediates the inhibition of protein extravasation resulting from stimulation of the trigeminal ganglia.

Sumatriptan exhibits low bioavailability and relatively short duration of action. Its affinity for a number of serotonin receptor subtypes gives rise to undesirable side effects, particularly vasoconstriction, which severely limits its utility in the treatment of migraine. The compounds of this invention, however, are highly bioavailable through several routes of administration including, but not limited to, oral, buccal, intravenous, subcutaneous, intranasal, intraocular, transdermal, rectal and by inhalation. They exhibit a rapid onset and long duration of action, typically requiring only a single dose per day to maintain therapeutic levels. Since compounds of this invention are potent agonists of the 5-HT$_{1F}$ receptor, extremely low doses are required to maintain therapeutic levels. Additionally, due to the high selectivity of compounds of this invention for the 5-HT$_{1F}$ receptor, complications due to vasoconstriction are avoided. Compounds of this invention also inhibit protein extravasation if administered prior or subsequent to stimulation of the trigeminal ganglia, suggesting they may be administered prior to an incipient migraine attack to prevent pain, or during a migraine attack to alleviate pain.

The ability of agonists of the 5-HT$_{1F}$ receptor in general, and the compounds of the present invention specifically, to alleviate pain is demonstrated by testing in a standard model of chronic pain (Calvino, et al. *Behavioural Brain Research*, 24, 11–29 (1987); Colpaert, *Pain*, 28, 201–222 (1987)). For example, an arthritis like state can be produced in rats days after a single injection of Freund's Complete Adjuvant or a synthetic adjuvant like lipidal amine (N,N-dioctyldecyl-N', N-bis(2-hydroxyethyl) propanediamine) in oil (Benslay and Bendele, *Agents Actions* 34(1–2), 254–6, (1991); Bendele et al., *J. Pharmacol Exp Ther* 260(1), 300–5 (1992); Meacock et al., *Ann Rheum Dis* 53(10), 653–8 (1994)). Animals treated this way develop chronically swollen and painful hindpaws resulting in increased irritability, and decreased locomotion. The ideal analgesic would increase the exploratory activity of arthritic animals toward normal without increasing or decreasing this behavior in normal animals. Analgesic compounds, for example morphine and citalopram, have been demonstrated to improve exploratory behavior in these animals (Larsen and Arnt, *Acta Pharmacol Toxicol* (Copenh) 57(5), 345–51 (1985).

Analgesic Assay

Male Lewis rats (Harlan-Sprague Dawley, Inc., Indianapolis, Ind.) weighing about 225 grams are housed in clear plastic cages with ad lib access to chow and water. Rats are maintained under a 12 hours on and 12 hours off light cycle.

To produce polyarthritis, half of the rats are injected subcutaneously at the dorsal base of the tail with 7.5 mg/rat of lipoidal amine in 0.1 ml of Incomplete Freund's Adjuvant. This single lipoidal amine injection results in hindpaw inflammation which becomes obvious in about ten days. The other half of the rats receive vehicle injections. Eleven days after lipoidal amine or vehicle injection, animals are treated either orally or subcutaneously with test compound or water vehicle. One hour after treatment, individual animals are placed in activity monitors (Omnitech Electronics, Columbus, Ohio) which constitute a novel environment. The activity monitors have an "open field" area of 42×42 cm and, using infrared light beams and photocells, quantify exploratory behavior. This is accomplished using a grid of photosensors placed at floor level to measure horizontal activity. A computer analyzes the data from the sensor array. Exploratory behavior is quantified during the first 5 minutes in the chamber. The measured parameter used in this study is total distance traveled during the 5 minute test period.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, buccal, rectal, intranasal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., Remington's Pharmaceutical Sciences, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, scahets, cachets, elixirs, suspensions, emulsions, solutions, syrups, aerosols (as a solid or in a liquid medium), solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Compound of Example 8 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | (mg/tablet) |
|---|---|
| Compound of Example 2 | 25.0 |
| Cellulose, microcrystalline | 200.0 |
| Colloidal silicon dioxide | 10.0 |
| Stearic acid | 5.0 |

The components are blended and compressed to form tablets, each weight 240 mg.

Formulation Example 3

Suppositories, each containing 25 mg of active ingredient are made as follows:

| Ingredient | Amount |
|---|---|
| Compound of Example 4 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 4

An intravenous formulation may be prepared as follows:

| Ingredient | Quantity |
|---|---|
| Compound of Example 19 | 250.0 mg |
| Isotonic saline | 1000 ml |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well know in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. The compound of Formula IIa:

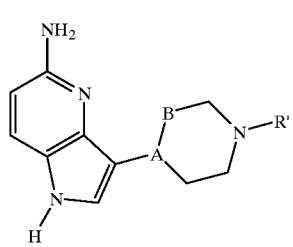

IIa where: A—B is —CH—CH$_2$—; R' is C$_1$–C$_6$ alkyl, (C$_1$–C$_4$ alkoxy)carbonyl, benzyl, or phenylethyl; and acid addition salts thereof.

2. The compound of claim 1 where R' is methyl.

* * * * *